US012264308B2

United States Patent
Raviv et al.

(10) Patent No.: US 12,264,308 B2
(45) Date of Patent: *Apr. 1, 2025

(54) SYSTEM AND METHODS FOR IMMUNE CELLS EXPANSION AND ACTIVATION IN LARGE SCALE

(71) Applicant: PLURI BIOTECH LTD., Haifa (IL)

(72) Inventors: Lior Raviv, Kfar Monash (IL); Shirley Bachar, Petach Tikva (IL); Dorina Roberman, Nahariya (IL)

(73) Assignee: PLURI BIOTECH LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/593,868

(22) Filed: Mar. 2, 2024

(65) Prior Publication Data

US 2024/0392225 A1   Nov. 28, 2024

Related U.S. Application Data

(62) Division of application No. 18/200,942, filed on May 23, 2023, now Pat. No. 11,939,562.

(51) Int. Cl.
   *C12M 1/12* (2006.01)
   *C12M 1/00* (2006.01)
   *C12N 5/078* (2010.01)

(52) U.S. Cl.
   CPC .......... *C12M 25/14* (2013.01); *C12M 23/02* (2013.01); *C12M 23/20* (2013.01); *C12M 25/18* (2013.01);
   (Continued)

(58) Field of Classification Search
   CPC ...... C12M 25/14; C12M 25/18; C12M 23/02; C12M 23/20; C12N 5/0634; C12N 2513/00
   See application file for complete search history.

(56) References Cited

U.S. PATENT DOCUMENTS

| 5,501,971 A | * | 3/1996 | Freedman | .............. C12M 23/34 |
|  |  |  |  | 435/399 |
| 11,939,562 B2 | * | 3/2024 | Raviv | ..................... C12M 23/02 |

(Continued)

FOREIGN PATENT DOCUMENTS

| WO | 2022066466 A1 | 3/2022 |
| WO | 2022076519 A1 | 4/2022 |

OTHER PUBLICATIONS

International Search Report of Jul. 24, 2023 for PCT/IL2023/050529.

*Primary Examiner* — Michael L Hobbs
(74) *Attorney, Agent, or Firm* — Maxwell L Minch Esq. PA; Maxwell L. Minch

(57) ABSTRACT

This invention discloses a three-dimensional (3D) bioreactor for large scale expansion of immune cells and methods of use. The 3D bioreactor comprising at least one packed bed chamber comprising at least one porous scaffold; at least one porous scaffold coated with one or more extra cellular matrix protein (ECM); at least one container comprising a fluid media, the fluid media is configured to flow through said packed bed chamber with at least one porous coated scaffold; and at least one population of immune cells suspended in the fluid media, wherein, the at least one porous scaffold coated with said ECM is creates a stationary niche having low shear forces that imitate the natural growth environment of the immune cells and allows expansion of the immune cells population that flow through the coated porous scaffold in large scale.

14 Claims, 21 Drawing Sheets

(52) U.S. Cl.
CPC ........ *C12N 5/0634* (2013.01); *C12N 2513/00* (2013.01)

(56) References Cited

U.S. PATENT DOCUMENTS

| | | |
|---|---|---|
| 2013/0039892 A1 | 2/2013 | Ltd |
| 2014/0227769 A1 | 8/2014 | Strobbe et al. |
| 2017/0037421 A1 | 2/2017 | Blessing et al. |
| 2021/0189329 A1 | 6/2021 | Foundation |

* cited by examiner

Day 7
After harvest

SYSTEM AND METHODS FOR IMMUNE CELLS EXPANSION AND ACTIVATION IN LARGE SCALE

CROSS-REFERENCE TO RELATED APPLICATIONS

This application is a divisional application from, and claims the benefit of, U.S. patent application Ser. No. 18/200,942 having a filing date of May 23, 2023 which was patented as U.S. Pat. No. 11,939,562 B2 on Mar. 26, 2024, and claims priority to U.S. Provisional Application No. 63/344,780, having a filing date of May 23, 2022, the disclosure of the foregoing is hereby incorporated by reference in its entirety and all commonly owned.

FIELD OF THE INVENTION

This invention is directed to a system and method for culturing and/or activating immune cells in a large scale. More particularly, the invention is directed to large scale culturing and/or activating of immune cells in packed bed bioreactors.

BACKGROUND

The culturing of mammalian cells is complicated on principle due to their high sensitivity, relatively slow proliferation, complex differentiating processes and the absolute sterility as a basic condition. Cells culturing in a large scale is always a challenging procedure. Even a small-scale growth of cells requires attention and specific knowledge as often serious problems are encountered. For example, cell cultures put under stress or damage during the cell culture preparation or testing procedures, and thus, any analysis based on the cultured cells may show results that are at least in part a consequence of such damage. Moreover, applying conclusions drawn from results obtained on damaged cells to the situation in vivo or usage of the cells for immunotherapy may cause fatal consequences. Furthermore, the damages or stressful conditions are not reproducible between individual cell cultures and may influence the growth of the cells. When approaching cell culturing in a large scale, these challenges become even more critical. In recent decades various attempts have been made. US Pat. App. No. 2006/0194320 describes a device and method for culturing cells and/or tissue that mimic cellular structures and immunological functions of immunologically active tissues, however, this system and method are limited to a volume of 4 ml. Additional patents and patent applications related to the field of this invention are U.S. Pat. Nos. 8,911,995, and 10,472,612.

In addition, the use of bioreactor for cells and tissue culturing is well known. A detailed overview on bioreactor design, prototyping and process control for reproducible three-dimensional tissue culture is provided in https://www.minerva-kg.de/libraryonline/upload/files/file_6400.pdf.

Cultivating immune cells in vitro is a further challenge. In recent years, the human immune system was harnessed as a foundation for therapeutic technologies capable of recognizing and killing tumor cells and has been the central objective of anti-cancer immunotherapy. Consequently, there has been an increasing interest in improving the effectiveness and accessibility of this technology to make it widely applicable for adoptive cell therapies (ACTs) such as chimeric antigen receptor T (CAR-T) cells, tumor infiltrating lymphocytes (TILs), dendritic cells (DCs), natural killer (NK) cells, and many others. However, to implement this technology, the currently available systems for culturing immune cells do not meet the need as they either damaging the cells, have low efficacy, have limited scale up ability, and some require very high costs (see: Ganeeva I. et. al. 2022 "Recent Advances in the Development of Bioreactors for Manufacturing of Adoptive Cell Immunotherapies", Bioengineering 2022, 9, 808. https://doi.org/10.3390/bioengineering9120808). In this paper, the main culturing methods known to date in the art for immune cells cultivation were reviewed as well as their advantages and disadvantages. In more detail, comparison was made between Stirred Flask, G-Rex flask, Rocking motion bioreactors, Stirred tank bioreactors, Hollow fiber bioreactors, and CliniMACS Prodigy. Thus, there is an urgent need for scalable, cost-effective, and GMP-compliant bioreactors for culturing immune cells.

The present invention is aimed to provide a system and method for large scale culturing and/or activating immune cells populations.

SUMMARY OF THE INVENTION

In one main aspect, the present invention is directed to a large-scale system and method for culturing and/or activating immune cells. The challenge to be solved for effective large-scale growth of immune cells is to avoid or minimize the high shear stress that may damage cells in order to obtain a high scale homogeneous system, and to create conditions that allows interaction between cells and activator and transfection agents, so as to create physical niche and conditions that allows high cell to cell interaction.

The present invention discloses in one aspect a method and a system for growing immune cells consisting of a porous stationary phase that is positioned within a flowing media. The stationary phase may be positioned within a bioreactor or can be positioned in a separate chamber that is functionally connected to a bioreactor. The porous element/s as will be described in detail hereinbelow are positioned within a basket of a packed bed bioreactor and are not mobile, and do not move with the liquid flow that surrounds them and flow through them. The stationary phase can be implemented in various forms and aimed to create an environment with low flow and low shear forces.

The terms "porous stationary phase", "porous scaffold/s", "porous element/s", and "porous coated scaffold" as used herein, are all directed to the same, and may be used in the description below interchangeably. In some embodiments, the porous stationary phase is coated with Extra Cellular Matrix (ECM), and it may further be coated with immune system cells activator/s, in order to activate and expand the immune cells. The combination of all components creates a niche for immune system cells that mimic their natural environment in tissues and lymph nodes.

The terms "Activator" and "Immune cell activator" as used herein, are all directed to the same, and may be used in the description below interchangeably. In some embodiments "Activator" and "Immune cell activator" is an antigen presenting cell loaded with antigen presented on the cell surface. In another embodiment, the activator is an antibody directed to an activation receptor on immune cell surface. In yet another embodiment the activator is an antigen conjugated to a molecule that can be presented to an activation receptor on immune cell surface.

The term "Niche" as used herein is directed to a stationary phase having pores, such as but not limited to scaffolds, beads, and carriers that allows liquids and particles to flow through it. The particles may be cells, or other components, either synthetic or natural.

The niche created is mimicking the lymph node/tissue in terms of the microenvironment in which the immune cells naturally grow, to bring about optimal cell growth. Furthermore, since the niche created imitates the natural environment of the cells, it allows to activate the cells such that only certain cells respond to the activation, and thus a certain selection is made for the desired cells.

Additionally, the niche created allows to grow the immune cells on a large scale while maintaining relatively low shear forces to minimize cell damage.

The terms "Media" and "Medium" are both intended to be synonymous and may be used interchangeably hereinbelow.

The terms "packed bed chamber", "packed bed basket", "basket", "growth basket" are all intended to be synonymous and may be used interchangeably hereinbelow.

Reference herein to "growth" of cells, or a population of cells, is intended to be synonymous with expansion of a cell population, culturing of cell population, with or without activation of the cells.

The terms "immune cells", "immune cells population" and "lymphoid cells" as used herein are all directed to the same and may be used in the description below interchangeably.

In certain embodiments, lymphoid cells are expanded without substantial differentiation. In various embodiments, the described expansion is on a 2D substrate, on a 3D substrate, or a 2D substrate, followed by a 3D substrate.

In some embodiments, the lymphoid cells are incubated in a bioreactor, non-limiting examples of which are suspension culture and culture on 3D carriers. The term "bioreactor culture" refers to culture in an apparatus (bioreactor), typically sterile, wherein the cells are maintained under controlled conditions as will be described hereinbelow with reference to FIG. 1.

Reference herein to "activation" of the immune cells, or a population of immune cells, is intended to be synonymous with exposure of immune cells to an antigen that causes a change in the cell morphology and triggers immune response detected by a rapid proliferation and secretion of variety of cytokines and chemokines.

Thus, in one main aspect, the present invention is directed to a three-dimensional (3D) bioreactor for large scale expansion of immune cells comprising: a) at least one packed bed chamber comprising at least one porous scaffold; b) at least one porous scaffold coated with one or more extra cellular matrix protein (ECM); c) at least one container comprising a fluid media, the fluid media is configured to flow through said packed bed chamber with at least one porous coated scaffold; and d) at least one population of immune cells suspended in the fluid media; wherein, the at least one porous scaffold coated with said ECM is configured to create a stationary niche having low shear forces that imitate the natural growth environment of the immune cells and allows expansion of the immune cells population that flow through the coated porous scaffold in large scale.

The at least one porous scaffold may further be coated or linked with at least one immune cells activator. In some optional embodiments, the immune cells activator is either one of an Antigen Presenting Cell (APC), either loaded with antigen or unloaded with antigen, or an antigen conjugated directly to the coated porous scaffold. In the scenario that the APC is unloaded with antigen, the antigen may be presented at a later stage upon desire to activate the immune cells.

In further options, the expanded immune cells may be further activated within the packed bed chamber upon exposure of the immune cells population to the at least one porous coted scaffold conjugated with the immune cells activator.

In another options, the expanded immune cells may be further activated within the packed bed chamber upon exposure to a suspended soluble immune cells activator and further expanded with at least one porous ECM coted scaffold.

In some embodiments of the invention, the expanded and/or activated immune cells population is either harvested or reactivated upon exposing the APC attached to the at least one coated porous scaffold to an antigen, to create additional activation signal to the immune cells population.

Yet, in some further embodiments, the immune cells population are either harvested or reactivated by transferring the expanded immune cells to a different bioreactor comprising at least one porous scaffold coated with a different or similar immune cells activator.

The porous scaffold may be a single porous scaffold matrix expanded within the packed bed chamber inner space, or it may be a plurality of mini or micro porous scaffolds filling the packed bed chamber.

In some further optional embodiments of the invention, the immune cells population is genetically modified by using gene modifying agents spiked into the bioreactor medium.

The present invention is further directed to a method for large scale expansion of immune cells in a three-dimensional (3D) bioreactor comprising: a) inserting at least one porous scaffold into at least one packed bed chamber; b) coating the at least one porous scaffold with one or more extra cellular matrix protein (ECM); c) circulating fluid media from at least one container, the fluid media is configured to flow through said packed bed chamber comprising the at least one porous coated scaffold; and d) suspending at least one population of immune cells in the circulated fluid media; wherein, the at least one porous scaffold coated with said ECM is configured to create a stationary niche having low shear forces that imitate the natural growth environment of the immune cells and to allow expansion of the immune cells population that flow through the at least one porous scaffold in large scale.

The method may further comprise a step of coating the at least one porous scaffold with at least one immune cells activator after step coating the scaffold with ECM and, a step of exposing the immune cells population to the at least one activator after suspending at least one population of immune cells in the circulated fluid media, so as to expand and activate the immune cells population within said packed bed chamber.

The method may further include a step of genetically modifying the immune cells inside the 3D bioreactor using gene modifying agents spiked into the fluid media.

In some optional embodiments, the method further comprise a step of harvesting the immune cells or portion of the cells, and further expansion and reactivating the immune cells population either in the same bioreactor or in a different bioreactor.

Additionally, or alternatively, the method described above may further comprise a step of harvesting the immune cells followed by a step of gene modification done outside the system and then reseeding the genetically modified immune cells into the same bioreactor or to a different bioreactor.

Yet, in a further aspect, the present invention is aimed to provide a three-dimensional (3D) bioreactor for large scale expansion and activation of immune cells population comprising: a) at least one packed bed chamber comprising at least one porous Antigen Presenting Cell Mimetic Scaffold (APC-MS); b) at least one APC-MS coated with one or more extra cellular matrix protein (ECM); c) at least one container comprising a fluid media, the fluid media is configured to flow through said coated porous APC-MS; and d) at least one immune cells population suspended in said fluid media; wherein, said at least one APC-MS creates a stationary microenvironment having low shear forces that imitate the natural growth environment of the immune cells population and allows large scale expansion and/or activation of said immune cells population that flow through it.

The immune cells population may be reactivated upon exposing the coated porous APC-MS to an antigen, to create additional activation signal to the immune cells population.

In some optional embodiments, the immune cells population is reactivated by transferring the cells to a different bioreactor comprising at least one coated porous APC-MS having a different or similar antigen.

In accordance with embodiments of the invention, the at least one porous APC-MS may be made of a single unit, expanded within the packed bed chamber inner space, or it may be a plurality of mini/micro porous APC-MS filling the packed bed chamber.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the embodiments of the invention only and are presented in the cause of providing useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3A-3D are schematic partial front view illustrations of packed bed bioreactor 100 of FIG. 1 in different stages of the growth process of the immune cells population, wherein FIG. 3A illustrates a primary stage in which the packed bed basket contains uncoated scaffolds; FIG. 3B illustrated the packet bed basket containing coated scaffolds and filled with ECM protein solution; FIG. 3C. illustrates the packed bed basket with the coated scaffolds of FIG. 3B further linked to at least one type of immune cell activator; and FIG. 3D illustrates the packed bed bioreactor with the coated scaffolds linked to one or more activators and with immune cells flowing in the medium.

DETAILED DESCRIPTION OF EMBODIMENTS

Figure 1:
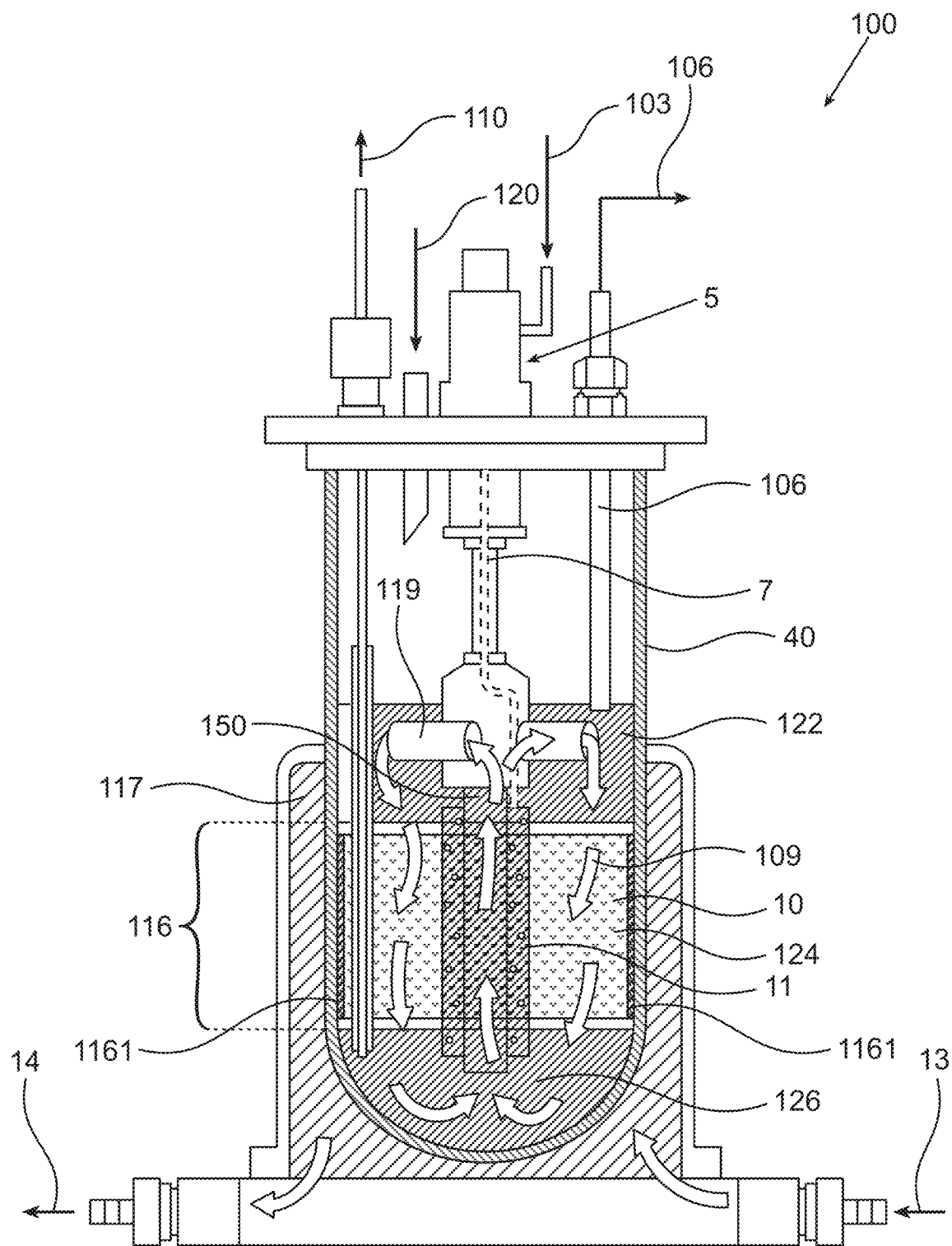
FIG. 1 is a schematic illustration of an optional packed bed bioreactor for growing, activating and harvesting immune cells populations according to embodiments of the invention.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is aimed to provide a system and method for large scale expansion and activation of various immune cells population.

In one main aspect this invention provides a 3D bioreactor for large scale expansion of immune cells comprising: a) at least one packed bed chamber comprising at least one porous scaffold; b) at least one porous scaffold coated with one or more ECM protein; c) at least one container comprising a fluid media, the fluid media is configured to flow through said packed bed chamber with at least one porous coated scaffold; and d) at least one population of immune cells suspended in the fluid media; wherein, the at least one porous scaffold coated with said ECM is configured to create a stationary niche having low shear forces that imitate the natural growth environment of the immune cells and allows expansion of the immune cells population that flow through the coated porous scaffold in large scale.

In a further aspect, this invention provides a method for large scale expansion of immune cells in a three-dimensional (3D) bioreactor comprising: a) inserting at least one porous scaffold into at least one packed bed chamber; b) coating the at least one porous scaffold with one or more extra cellular matrix protein (ECM); c) circulating fluid media from at least one container, the fluid media is configured to flow through said packed bed chamber comprising the at least one porous coated scaffold; and d) suspending at least one population of immune cells in the circulated fluid media; wherein, the at least one porous scaffold coated with said ECM is configured to create a stationary niche having low shear forces that imitate the natural growth environment of the immune cells and to allow expansion of the immune cells population that flow through the at least one porous scaffold in large scale.

Yet, in one further aspect, this invention provides a 3D bioreactor for large scale expansion and activation of immune cells population comprising: a) at least one packed bed chamber comprising at least one porous APC-MS; b) at least one APC-MS coated with one or more ECM protein; c) at least one container comprising a fluid media, the fluid media is configured to flow through said coated porous APC-MS; and d) at least one immune cells population suspended in said fluid media; wherein, said at least one APC-MS creates a stationary microenvironment having low shear forces that imitate the natural growth environment of the immune cells population and allows large scale expansion and/or activation of said immune cells population that flow through it.

The main aspects of this invention and optional ways to practice this invention will be better understood by the detailed description below of various exemplifying non-limiting drawings and examples described hereinbelow. Reference is now made to the drawings:

FIG. 1 is a schematic cross section view illustration of an optional packed bed bioreactor 100 for growing, activating and harvesting of immune cells populations according to embodiments of the invention.

Figure 2:
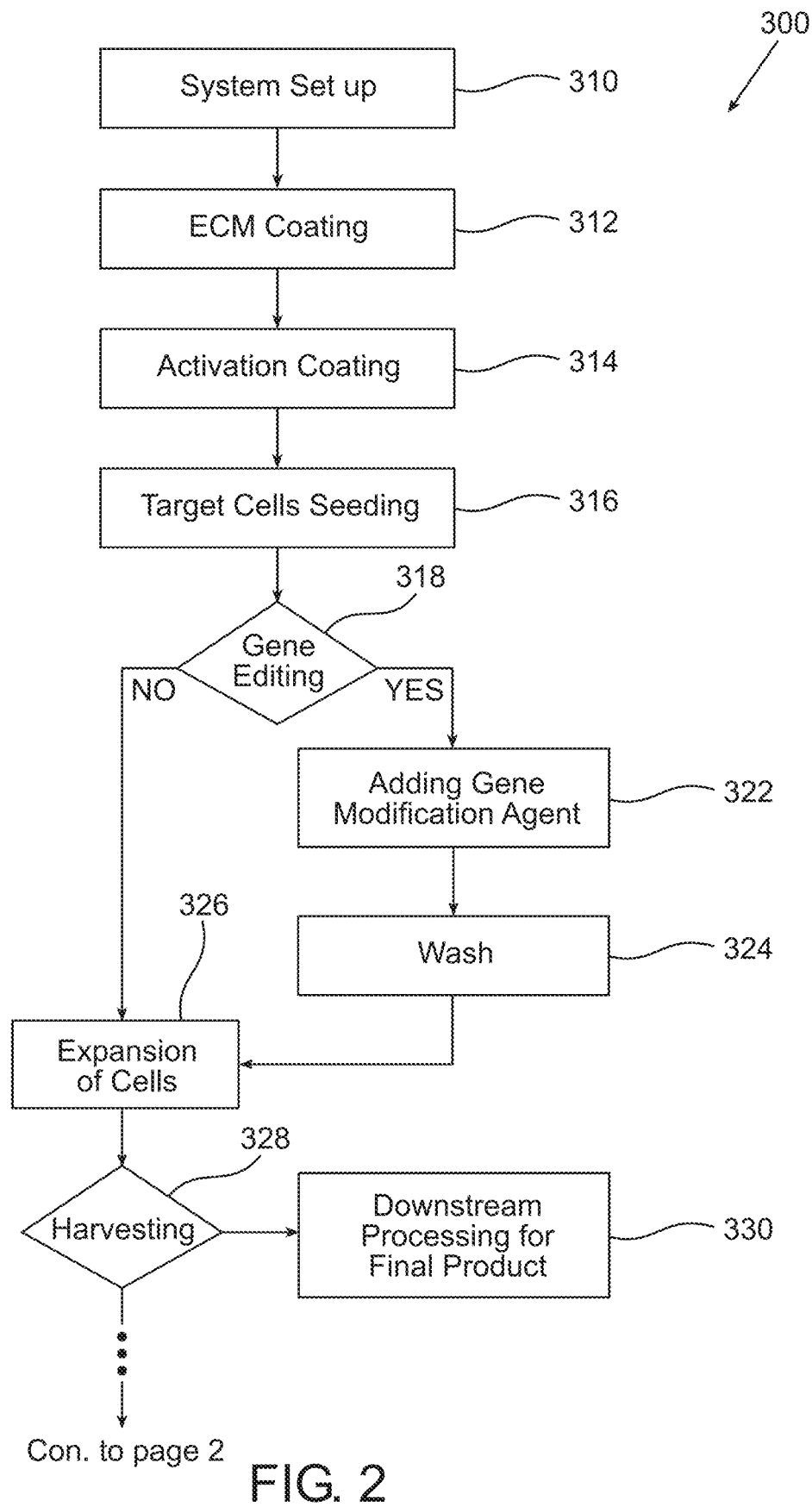
FIG. 2 is a flow chart diagram describing in high level the principal steps sequence for preparing and using a packed bed bioreactor for activating, expanding and harvesting immune cells.
Figure 2:
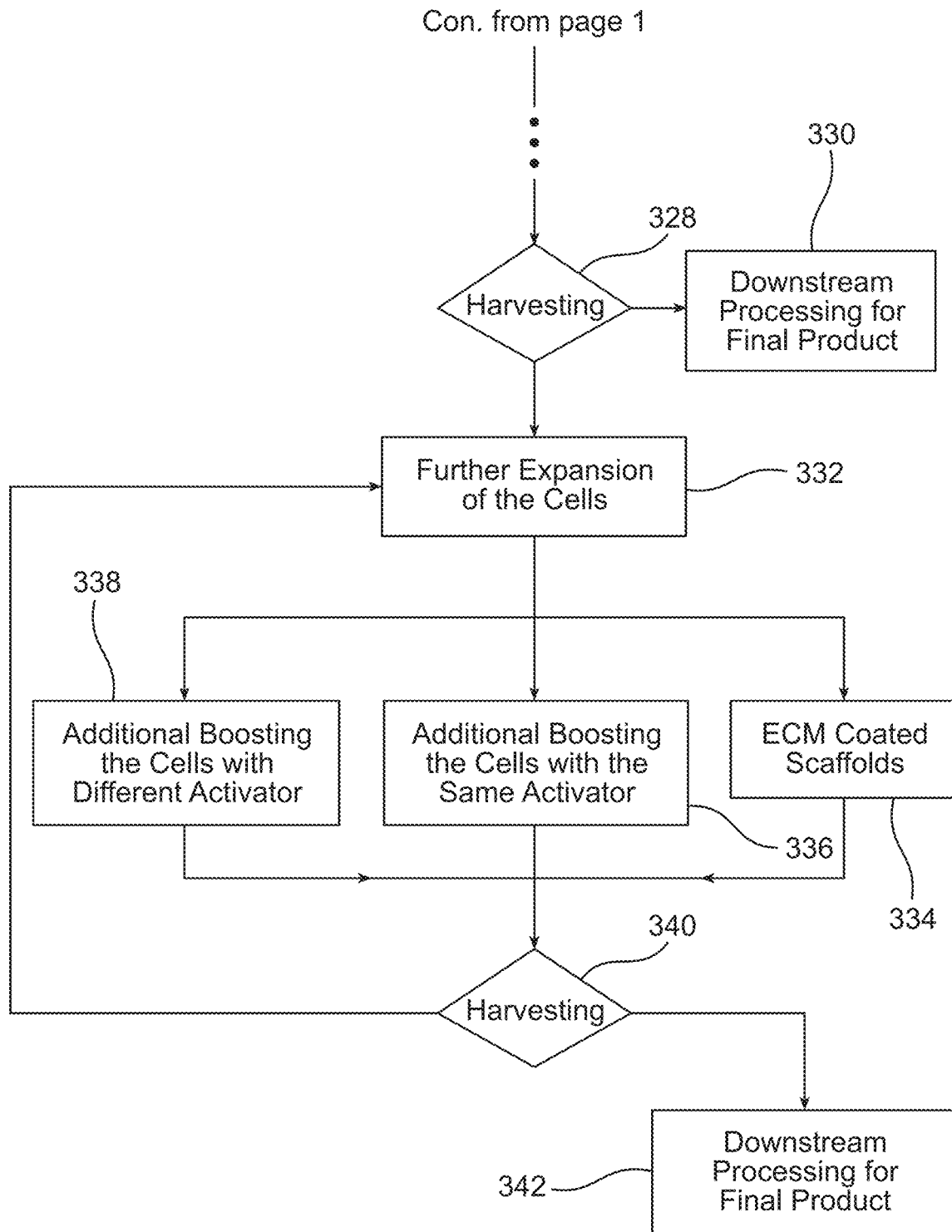

In the depicted embodiment, a growth and vibrating chamber 116 (denoted hereinafter: "basket") is loaded with at least one porous scaffold 10. The terms "carrier/s" and "scaffold/s" may be used interchangeably and are both refer to porous elements configured to be coated as will be described in detail with reference to FIG. 2 and to create a stationary niche within the basket that reduce the shear forces and mimic the natural environment of the immune cell populations. Basket wall 1161 is preferably separated from the bioreactor inner wall 40 and can be moved upward and downward. Bioreactor 100 is liquid media via an inlet pipe 120 that is configured and operable to deliver various media into the bioreactor, and then optionally be autoclaved. In other embodiments, following sterilization, the liquid is replaced with growth medium, which saturates basket 116 and its content. Basket 116 practically divides the fluids within bioreactor 100 into three main sections: upper section 122 that mainly comprises fresh media inserted via inlet pipe 120, middle section 124 that contains the media within basket 116 surrounding the coated scaffolds, and lower section 126 that mainly comprises media that flowed through the basket, and compared to the fresh media at upper section 122 it is usually poor of nutrients that were consumed by the immune cells at the middle section where their flow rate is decreased as they flow through the at least one porous coated scaffold, interact with other cells, and/or activated, and is rich with compounds and debris that are secreted by the immune cells. In the embodiment described herein, the media at the upper section 122 is being stirred by impeller 119 that creates movement of the fluid as depicted by arrows 109. In still further embodiments, various parameter such as, temperature, pH, dissolved oxygen concentration, and else, are set at the beginning of the process as the system set up procedure (see flow at FIG. 2 below), and constantly adapted to the suspension conditions as needed. In yet further embodiments, a slow initial stirring rate of the medium is used to promote cells adhesion to the coated scaffolds, then the stirring rate may increase. If desired, the cells may be harvested from the medium either for processing final product manufacturing or for further expansion of the immune cells as described in detail below (FIG. 2). In some embodiments, rotation of impeller 119 creates negative pressure in draft-tube 150, which pulls the media with the cells from lower section 126 through draft tube 150, then through impeller 119 ports into upper section 122, thus causing the medium and the immune cells to circulate in the direction according to arrows 109 uniformly in a continuous loop. In still, further embodiments of the invention adjustment of the media can be made by monitoring various parameters via electrode 106 so as to control the medium various parameters. In some optional embodiments, a ring sparger (not visible), is located inside the impeller aeration chamber 11, for oxygenating the medium flowing through impeller 119 ports, via gases added from an external port 103, which may be kept inside a housing 5, and a sparger line 7. In some other optional embodiments, gases may be added through inlet 120. Alternatively, sparged gas may be confined to a remote chamber and be absorbed by the nutrient medium, which washes over the system. In some optional embodiments, a water jacket 117 is coating media area within bioreactor 100, with ports for moving the jacket water in 13 and out 14. Removal pipe 110 is positioned along the bioreactor and has an opening within lower media section 126 to allow, if desired, to harvest the immune cells from the medium below basket 116. Removal pipe 110 may also be used to remove debris, and for refreshing the media upon partial removal of the used media and addition of fresh media.

In some embodiments, a continuous stirred tank bioreactor may be used, where a culture medium is continuously fed into the bioreactor and a product is continuously drawn out, to maintain a time-constant steady state within the bioreactor. A stirred tank bioreactor with a fibrous bed basket is available for example from New Brunswick Scientific Co., Edison, NJ). Additional bioreactors that may be used, such as but not limited to, stationary-bed bioreactors, perfusion bioreactors with polyactive foams, radial-flow perfusion bioreactors containing tubular poly-L-lactic acid (PLLA) porous scaffolds and any other bioreactors known in the art that are suitable for the purposes of the present invention. A "stationary-bed bioreactor" refers to a bioreactor in which the cellular growth substrate is not ordinarily lifted from the bottom of the incubation vessel in the presence of growth medium. For example, the substrate may have sufficient density to prevent being lifted and/or it may be packed by mechanical pressure to prevent it from being lifted. The substrate may be either a single body or multiple bodies. Typically, the substrate remains substantially in place during the standard agitation rate of the bioreactor. In some embodiments, multiple carriers are loosely packed, for example forming a loose packed bed, which is submerged in a nutrient medium.

Yet, in certain embodiments, a perfused bioreactor is used, wherein the perfusion chamber contains a 3D substrate. In certain embodiments, the 3D substrate is in the form of porous scaffolds 10. The porous scaffold may be made of a single large unit encompassing the entire volume or most of the volume of the packed bed chamber. Alternatively, the porous scaffold in use may be a plurality of mini particles. In some further optional embodiments, the porous scaffolds, may be for example, macro carriers, microcarriers, or a mixture thereof. Non-limiting examples of carriers that are available commercially include alginate-based (GEM, Global Cell Solutions), dextran-based (Cytodex®, GE Healthcare), collagen-based (Cultispher®, Percell Biolytica), and polystyrene-based (SoloHill Engineering) microcarriers.

In certain embodiments, T cells are incubated in a bioreactor with "APC-MS", a term used herein to refer to a scaffold (which may be, in more specific embodiments, any scaffold mentioned herein) attached or associated with lymphocyte activating moieties, more specific embodiments of which are fibrous carriers or mesoporous silica micro-rods that are attached to or coated with activating moieties.

The term packed-bed bioreactor, except where indicated otherwise, refers to a bioreactor in which the cellular growth substrate is not ordinarily lifted from the bottom of the incubation vessel in the presence of growth medium. For example, the substrate may have sufficient density to prevent being lifted and/or it may be packed by mechanical pressure to present it from being lifted. The substrate may be either a single body or multiple bodies. Typically, the substrate remains substantially in place during perfusion at the standard perfusion rate of the bioreactor. In certain embodiments, the definition does not exclude that the substrate may be lifted at unusually fast perfusion rates, for example greater than 200 rpm.

In other embodiments, a biocontainer is used to expand the cells, which is, in further embodiments, adapted for suspension culture. In various embodiments the biocontainer is used for and/or adapted for batch, fed-batch, or continuous culture.

FIG. 2 is a flow chart diagram describing in high level the principal steps sequence for preparation and usage of a packed bed bioreactor system, for expanding, activating and harvesting immune cells populations in accordance with embodiments of the invention.

The system set-up step 310 includes the assembly of the system, packing of the bioreactor basket with porous scaffolds in the desired amount, connecting the desired electrodes for the monitoring and control of the culture parameters (e.g., pH, dissolved oxygen, temperature) during the use of the system, connecting necessary tubing for fresh nutrients supply and byproduct removal, sealing and performing integrity tests and sterilization of the system by steam sterilization in autoclave. Following the sterilization, the system is connected to a bioreactor control station and the electrodes are calibrated.

The porous scaffolds also denoted hereinbelow "carriers" may be made of natural materials or synthetic materials and may have various dimensions. Some none limiting examples of carriers that are available commercially including alginate-based (GEM, Global Cell Solutions), dextran-based (Cytodex®, GE Healthcare), collagen-based (Cultispher®, Percell Biolytica), and polystyrene-based (SoloHill Engineering) carriers. Alternatively, or in addition, the scaffolds may comprise a fibrous material, optionally an adherent fibrous material, which may be, for example, a woven fibrous matrix, a non-woven fibrous matrix, or either. Non-limiting examples of fibrous scaffolds are polyester mesh-containing carriers such as New Brunswick Scientific Co.™ Fibra-Cel® disks, available commercially from Eppendorf™ AG, Germany, and including a polypropylene support; and microporous carriers such as BioNOC™ II carriers, available commercially from CESCO BioProducts (Atlanta, GA) and made of PET (polyethylene terephthalate). In certain embodiments, the referred-to fibrous matrix comprises a polyester, a polypropylene, a polyalkylene, a polyfluorochloroethylene, a polyvinyl chloride, a polystyrene, or a polysulfone. In more particular embodiments, the fibrous matrix is selected from polyester and a polypropylene.

In order to create an environment that mimics the natural environment of the immune cells, the ECM coating step 312 is performed. In this step, by using the hydrophilic end group on the Fibra-Cel® disks, coating the scaffold with different materials is applicable by simply submerging the scaffold in a solution containing ECM proteins in order to create electrostatic interactions. Detailed description of the extracellular matrix effect on immune cells is provided in Sutherland T. E et al., "*The extracellular matrix and the immune system: A mutually dependent relationship*", Science. 2023 Feb. 17; 379 (6633); PMID: 36795835. It should be clear that other scaffolds may be used and the described Fibra-Cel® disks are a non-limiting example. Additionally, coating the scaffolds may be carried out with natural ECM components or synthetic ECM components.

In this way, for example, different proteins such as but not limited to Albumin, Fibronectin, Fibrin, Fibrinogen, Collagen, Hyaluronan, Elastin, Laminin, Selectin and else, can be used to coat the scaffolds and create an environment similar to a natural environment. For example, in order to mimic the structure of a lymph node, scaffold can be coated with type III collagen that is the main building block of Reticular fibers that are the main components of the lymph node ECM. Furthermore, different organs have different combinations of the ECM proteins and therefore different combinations or concentrations can be used for coating. In a different embodiment, adhesion molecules can be conjugated to the scaffolds or to the proteins coating the scaffolds in order to facilitate stronger interaction between immune cells and the ECM coated scaffolds. For example, E-selectin, P-selectin, ICAM1, ICAM2 and VCAM1 are known in the art to be facilitators of the interaction between Leukocytes and ECM and help in the direction of Leukocytes to inflamed tissues. Based on that, coating the scaffolds with these molecules may increase the interaction between the Leukocytes and the ECM coated scaffolds. Alternatively, the ECM coating (step 312) occurs subsequently to the system set up (step 310) and followed by activation coating step of the scaffold (step 314). In different embodiments (depending on the product and its activating ligand) the activation coating step of the porous scaffolds (step 314) occurs after the ECM coating (step 312).

Step 314 describes the section where the scaffolds are coated with immune cells activating ligand. Section 314 can be performed before or after 312. Immune cells need to be activated by an antigen presentation usually occurring in the lymph node or in the infected tissue. By coating the scaffolds with ECM components and providing antigen presentation in a low sheer environment the niche created mimics the natural environment in which the activation occurs. In one embodiment, after the ECM coating with serum ECM proteins, adherent or semi adherent cells can attach to the fibers composing the scaffolds. Since some of the immune cells need interaction with an antigen presented by antigen presenting cells (APC) in order to be activated, antigen loaded APC's are seeded during step 314 after the coating step 312. The APC's adhere on the scaffolds and can present the antigen to different immune cells such as T cells, B-cells and all their subpopulations. In a different embodiment, APC's can be seeded into the bioreactor and adhere on to the scaffolds in a non-antigen presentation form and then after the cells adhered the antigen can be spiked into the medium filling the bioreactor in order to be presented for immune cells such as T cells and B cells. A more specified example of this embodiment is the use of monocytes for activating Mucosal-associated invariant T cells (MAIT). In this example, PBMC's are seeded into the bioreactor after the scaffolds were coated with fetal bovine serum proteins, monocytes adhere on the scaffolds and the rest of the cells are suspended in the media. Following the initial cell seeding 5-OP-RU (5-(2-oxopropylideneamino)-6-D-ribitylaminouracil) (the antigen for the activation of MAIT) is spiked into the medium in order to be presented by the monocytes and specifically activate the MAIT cells. In a different embodiment of this invention activation of immune cells can be moderated by an antigen that is conjugated onto the scaffold without APC's. The antigens can be antibodies for specific activation receptors on immune cells, proteins that are recognized by activation receptors such as TCR and more. For example, scaffolds were coated with both monoclonal anti-CD3 (OKT3) antibodies and anti-CD28 (CD28.2) antibodies, to provide a co-stimulatory signal that engages the T cell receptor. After an incubation period, a blocking step is performed followed by a wash step. After the wash step, coating of the scaffolds with fetal bovine serum proteins is performed. When medium is replaced and PBMC's are seeded into the bioreactor, cells are activated by interaction with the ECM and antibodies coated scaffolds.

One another example is the use of MR1 monomers, tetramers and other forms loaded or not loaded with 5-OP-RU for activating MAIT cells. When non 5-OP-RU loaded MR1 was used, the spiking of 5-OP-RU occurs after the blocking and wash steps are performed.

Step 316 describes the part of the seeding of cells including the target cells for activation and expansion. In this step, different sources of immune cells can be used for seeding the target cells i.e. PBMC's, collected from blood apheresis, PBMC's isolated from specific organs or tumors. Immune cells can be used fresh or frozen. In this step the immune cells are seeded into the bioreactors. Using different environmental parameters, such as but not limited to, agitation speed, PH, dissolved oxygen, temperature and else, the cells can either adhere or remain suspended in the bioreactors. The adherent cell can enter into the packed bed chamber, interact with the ECM proteins on the coated scaffold, and create a cellular organized microstructure inside the packed bed. In accordance with this embodiment, APC's may be seeded into the bioreactor and adhere onto the scaffolds in a non-antigen presentation mode, and create an environment mimicking the lymph node until activation occurs. A more specified example of this embodiment is the use of monocytes in order to activate Mucosal-associated invariant T cells (MAIT). In such example, PBMC's were seeded in the bioreactor after the scaffolds were coated with fetal bovine serum proteins, monocytes adhere on the scaffolds and the rest of the cells are suspended in the media. The non-adherent cells may remain suspended in the bioreactor, within the mobile phase, and migrate into or out of the packed bed chamber, to create cell to cell interaction with the adherent cells.

After seeding the immune cells at step 316, a decision shall be taken whether to conduct gene editing to the expanded cell population or not (step 318). If no gene editing is conducted, moving to step 326.

Step 326 describes the expansion phase of the target cells, in which the environmental parameters such as agitation speed, PH, dissolved oxygen, temperature and else are controlled. In this step, the bioreactor is constantly heated, and a pre-set mixture of gases is provided into the system, in order to maintain the desired conditions within the pre-determined desirable range. Once the cells are seeded and the activation occurs, either by APCs with loaded ligand or by scaffold/s coated with activating agents (antibodies), a state of infection is simulated in the bioreactor and a series of mechanisms are triggered, that cause clonal expansion of antigen-specific immune cells, during which the antigen-specific immune cells massively expand and up to ~90% of the total immune cells may become antigen specific. To support the rapid expansion of the immune cells an adequate supply of nutrients and removal of inhibitory metabolites are done, without disturbing the local microenvironment. In certain embodiments, the bioreactor may operate in a batch mode, fed batch mode, and/or perfusion mode. In another embodiment of the invention, a perfusion system (TFF, ATF, BioSep etc.) may be connected to the bioreactor. Using the perfusion system, the medium from the bioreactor can be replaced without the extraction of cells from the system. The perfusion system allows removal of conditioned medium out of the system, separating the suspended cells from the conditioned media and in parallel, supplying fresh medium into the bioreactor by command from a level electrode, weight, according to a pre-set flow rate or manually. In this example, the conditioned medium is sampled daily to measure the number of suspended cells and the concentration of essential substrates in the medium, according to the amount of cells and the concentration of the nutrients, The quantity of fresh medium to be supplied is calculated.

In step 328, the medium together with the immune cells are drained from the system for harvesting the target cells and the wash step preferably continues outside the bioreactor system. In this embodiment the medium replacement step can be done using batch centrifuge or continues flow centrifuge (kSep, unifuge and the like). Following the media replacement, the cells or part of the cells may be returned into a bioreactor to continue expansion with fresh growth medium at step 332. Alternatively, the harvested cells may be transferred at step 330 to downstream processing of the immune cells for final product manufacturing.

If gene editing is conducted to the target cells, at step 322, the immune cells are genetically modified in order to add or delete specific traits. Modifications such as the addition of new targeted or activation receptors or the deletion of specific receptors for self-recognition or the deletion of unwanted target receptors are used for transforming the immune cells for better treatments in different indications. In this step (322), gene modification agents may be inserted into the bioreactor by either non-viral agents such as liposomes (lipofectamine etc.), polymers (PEI etc.) or an electroporation process as described hereinbelow, or by viral vectors such as Retrovirus, Lentivirus, Adenovirus, Adeno-Associated virus or others. These gene modification agents can be loaded with either RNA or DNA constructs that can add new data into the genome or delete using methods such as CRISPR/Cas9, transposomes (sleeping beauty, PiggyBac) and DNA binding domain (Zinc finger domain etc.) In these embodiments, following the scaffold coating (312, 314), cell seeding (316) activation and during the cell expansion (326), the gene modifying agents such as viral vectors are spiked into the bioreactor medium. At this stage the agitation and other environmental parameters such as PH and temperature may be modified in order to prepare the cells for better penetration by the gene modifying agents. After the spike, an incubation period is employed under the appropriate conditions in order to allow the penetration of the gene modifying agents to the cells.

Yet, in some optional embodiment, the activated immune cells can be harvested from the bioreactor according to step (328) and aseptically transferred to an electroporation or to other 2D flasks device in order to allow the penetration of the gene modifying agents into the cells at step 322 by electroporation or viral and nonviral methods. In this embodiment, following the incubation period, the immune cells can be re-seeded into the bioreactor for the wash step or perform the wash step in the 2D flask.

Following the incubation period, the wash step 324 is initiated. During the wash step (324) the medium in the bioreactor is replaced a few times in order to extract the gene modifying agents from the system. In one embodiment of this invention, a perfusion system (TFF, ATF, BioSep and the like) is connected to the bioreactor. Using the perfusion system medium from the bioreactor can be replaced without the extraction of cells from the system. The perfusion system transfers out the old medium and in parallel, new medium is injected into the bioreactor by commend from a level electrode, weight or manually. This process may be performed for several chamber volumes until no gene modifying agent is found in the extracted medium. Alternatively, the medium with the cells and the gene modifying agents are drained or harvested from the system in step 328 following expansion of the cells (step 326), and the wash step continues outside the bioreactor. In this embodiment the medium replacement step can be done by using batch centrifuge or continues flow centrifuge (e.g. kSep, Unifuge). Following the media replacement, the cells may be reseeded into the starting bioreactor or into a new bioreactor (332) for further expansion.

Upon reaching the expansion duration time or reaching the needed concentration of immune cells for the desired end product or for seeding the cells to a larger scale bioreactor a cell harvesting step (328, 340) is performed. In one embodiment, the harvesting step is made by simply draining the medium with or without agitation out of the system. In a different embodiment the packed bed basket is connected to a harvesting system as described in detail in WO 2012/140519 of the same applicant, incorporated herein in its entirety by reference, and then during the drainage step slow vibration of the scaffold basket is performed in order to release trapped suspended immune cells from the packed bed scaffold niche created without causing physical damage to the cells. Furthermore, in all embodiments of the harvest step, cycles of medium re-filling and draining can be performed in order to collect all the cells from the system. In each cycle the extracted cells are drained into a sterile collection element for further processing.

In one further embodiment of this invention, at the end of the harvesting step (328,340) the cells or part of the harvested cells are further downstream processed (330, 342) for final product manufacturing. This step includes concentration and wash steps done using different systems such as continues flow centrifuges, filters, acoustic filtration devices and more. The concentration and wash steps are followed by specific cell collection steps using variety of separation methods and or final formulation of the product followed by filing of the end product into its final packaging (vials or cryobegs).

Yet, in a different embodiment of this invention, following the harvest step the harvested immune cells or partial portion of the harvested cells are used for further expansion (332). The further expansion is done by performing step 316 in the existing bioreactor or transferring the cells to a larger scale bioreactor for example a 1.5 L bioreactor with 30 g scaffold, a 3.5 L bioreactor with 100 g scaffold or 10 L bioreactor with 375 g of scaffold. Furthermore, the purpose of the new bioreactor can be utilized only for expansion using ECM coated scaffold (step 334), or to perform another activation step in order to reactivate the cells. Reactivation can be done with the same activator (step 336) in a new bioreactor for example, or it can be performed with a new activator in a new bioreactor (step 338). In both optional embodiments the new bioreactors are pre-prepared according to steps 310 to 314 described above.

In a different optional embodiment, the reactivation of the target cells may be performed either in the first bioreactor or in a new bioreactor by adding a soluble activator such as transact or anti CD3 and anti CD28 antibodies or by adding a soluble antigen that can be presented by APC's if they are already located in the bioreactor.

Figure 3A:
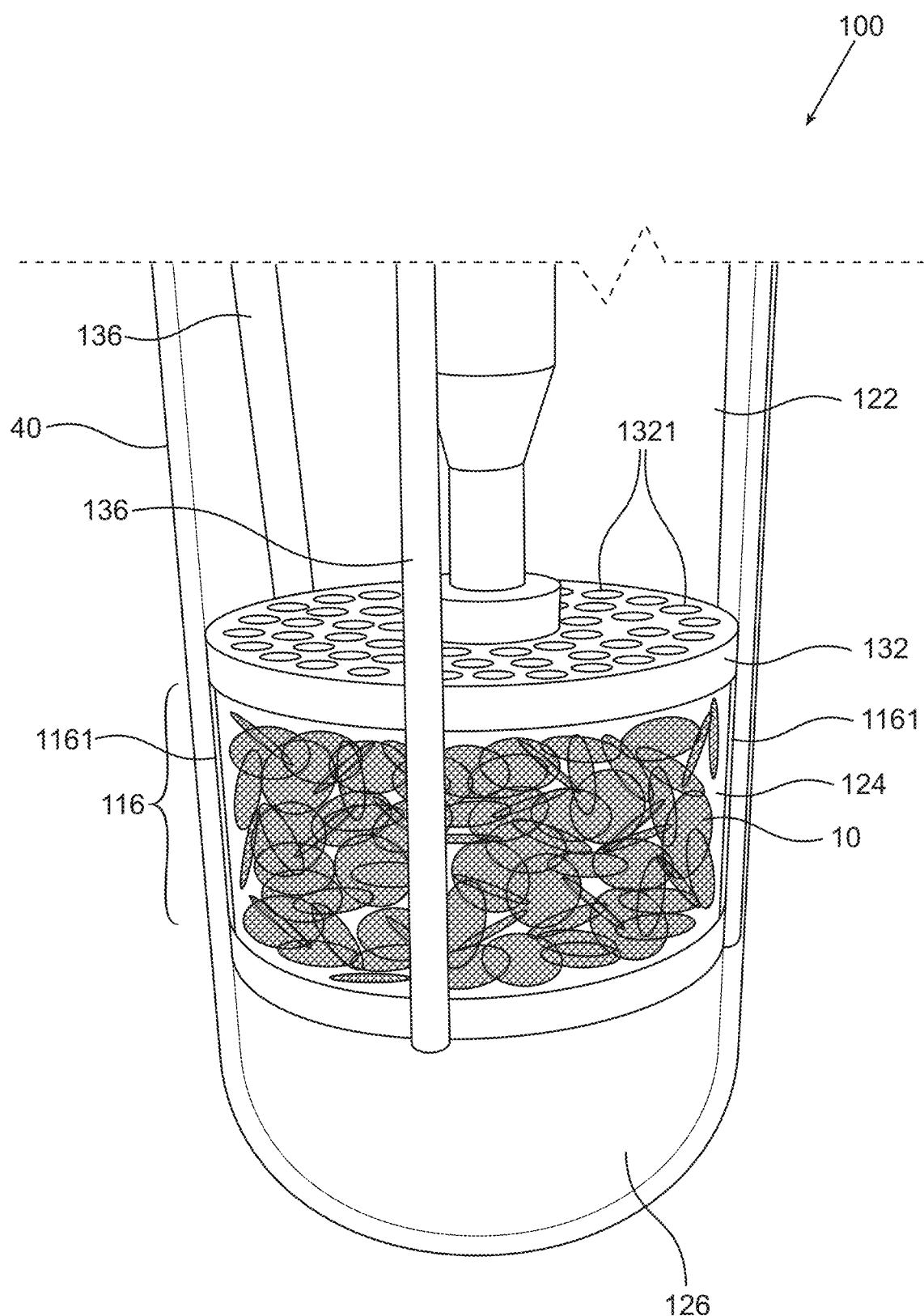

FIGS. 3A-3D are schematic partial front view illustrations of a packed bed bioreactor in different stages of the culturing process of the immune cells. FIG. 3A illustrates the set up stage of the system in which the packed bed basket 116 of bioreactor 100 contains only uncoated porous scaffolds 10.

In more detail, the top and bottom borders of the packed bed chamber 116 are composed of perforated discs 132 each having a plurality of holes 1321 in a predefined diameter/s. Perforated disc 132 is also denoted hereinafter: "disc", "grid", "upper grid", lower grid", "middle grid" all can be used interchangeably and directed to the upper, middle or lower walls of basket 416. In some optional embodiments, as described in detail with reference to FIG. 2 above, porous scaffolds are inserted into basket 116 and may occupy partial volume or most volume of the basket. At this stage, bioreactor 100 may be empty of liquids. Basket 116 is preferably connected to one or more vibrating rods 136 configured to allow vertical movement of basket 116. Vibration of basket is 116 may be used for harvesting the target cells during or at the end of the expansion process as described in FIG. 2. Basket 116 has a separate wall 1161 from bioreactor 100 wall 40 so as to allow upward and downward movement of the basket while maintaining the flow direction of the media with the target cells only through the upper and lower discs 132. Basket 116 is positioned within bioreactor 100 above the bottom of the bioreactor such that upper section 122 and lower section 126 are delimiting the middle section 124 that comprises the packed bed basket 116.

Figure 3B:
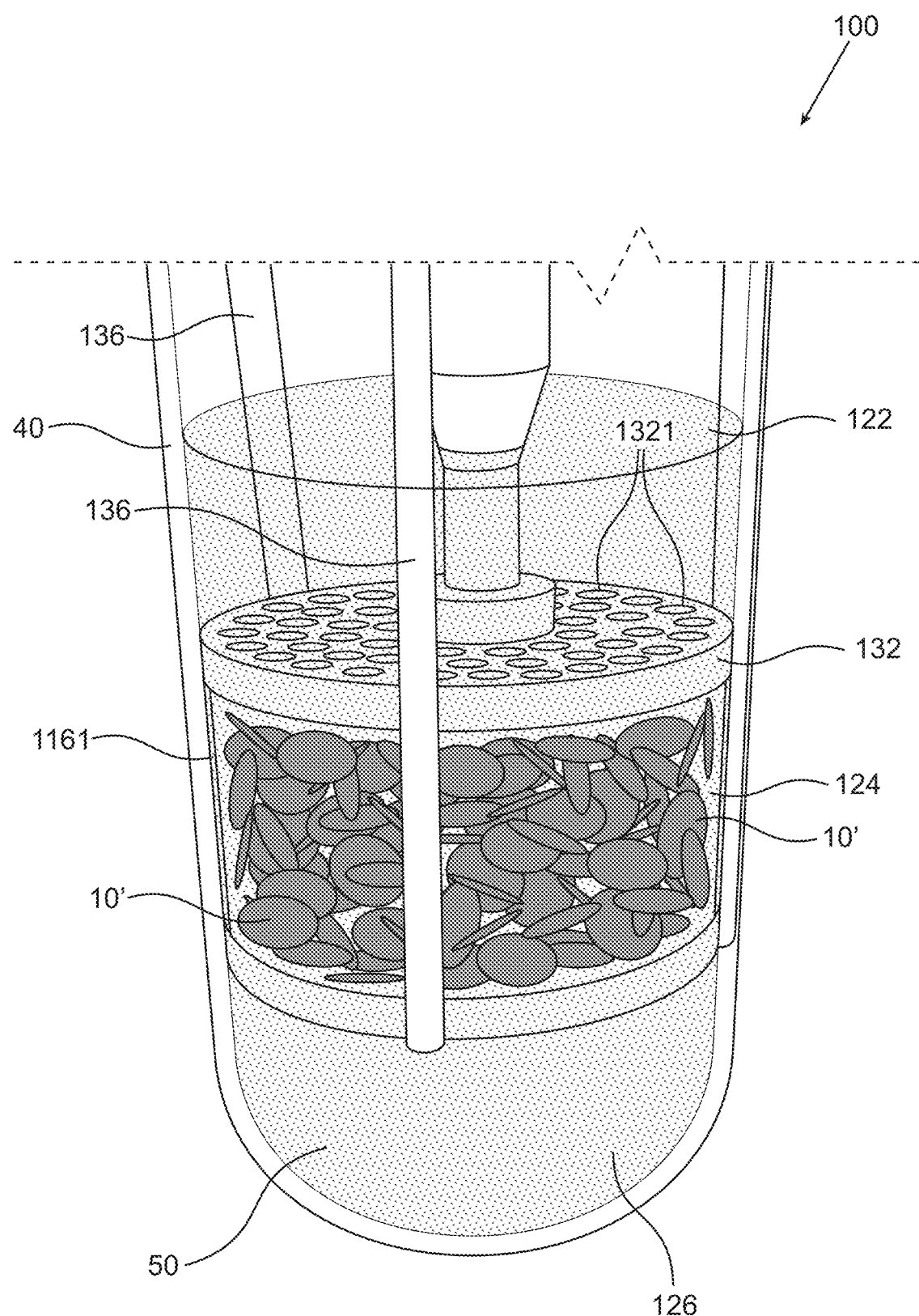
Figure 3C:
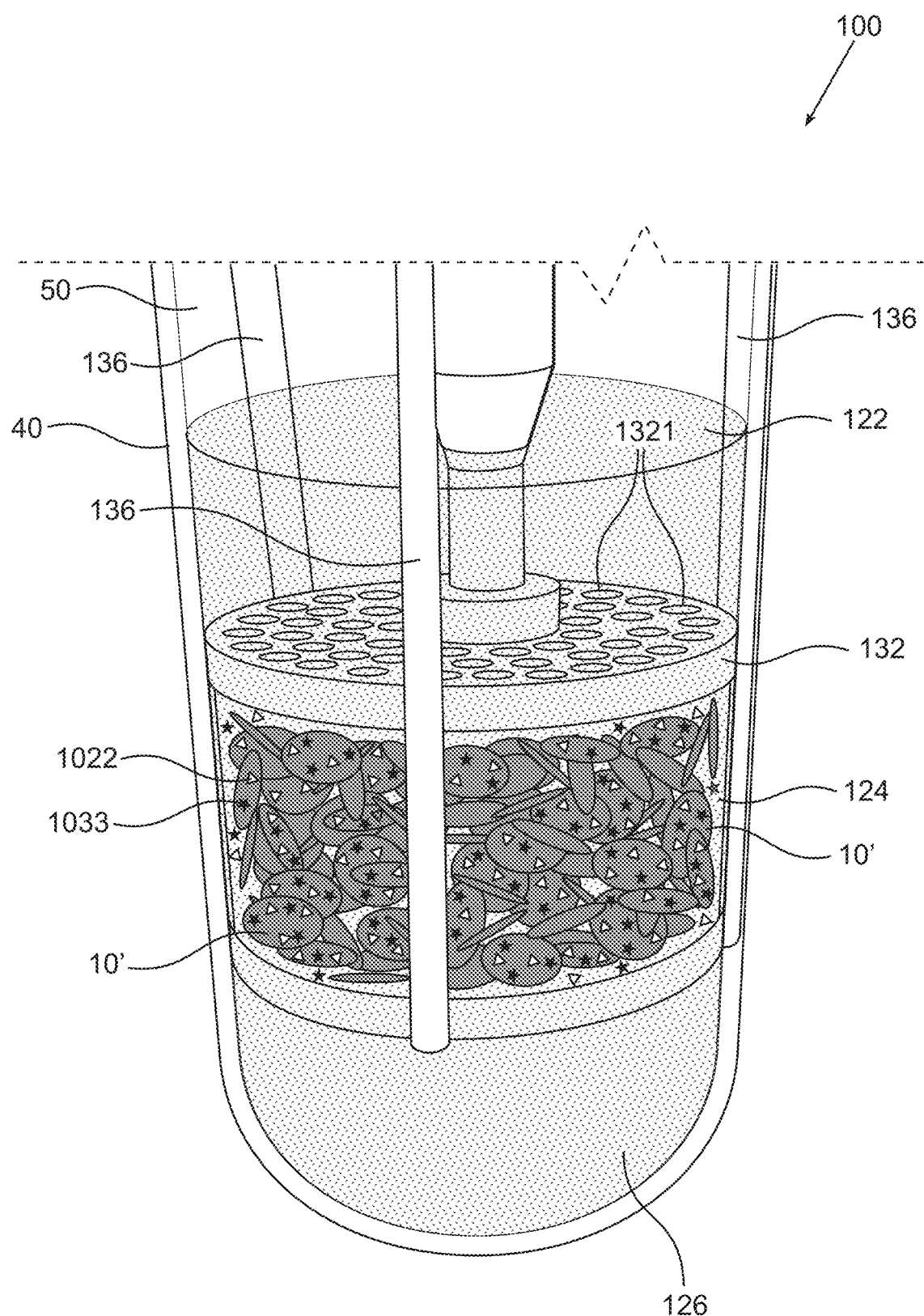
Figure 3D:
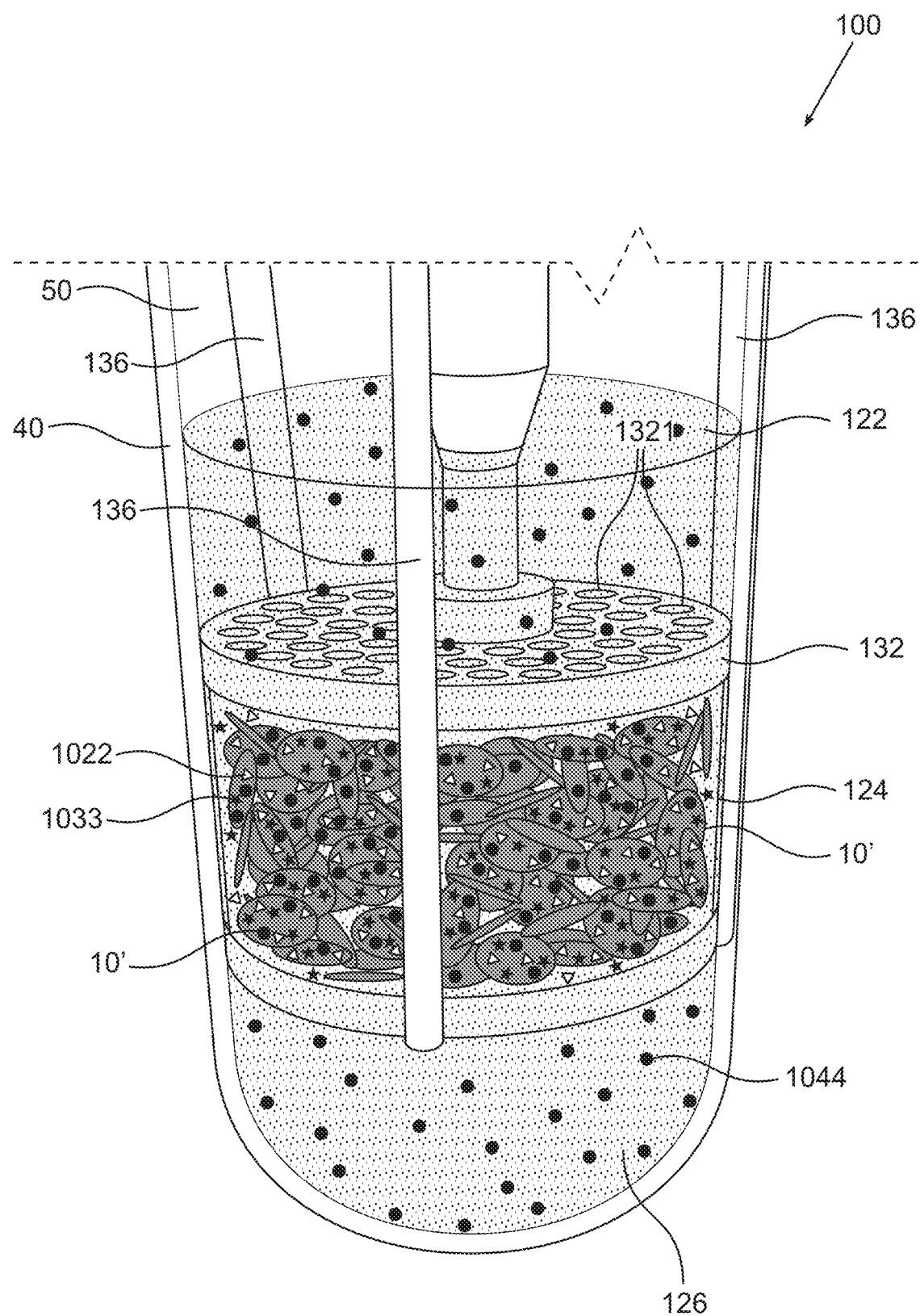

FIG. 3B illustrated packet bed basket 116 containing coated scaffolds 10' and filled with liquid medium 50. In order to create an environment suitable to mimic the natural environment of the immune cells population, the porous scaffold should first be coated with an ECM coating as described in detail in FIG. 2 above and in the examples of this invention. After ECM coating is performed, porous scaffolds 10' may be further coated or linked to at least one type of antibody 1022 or to an Antibody Presenting Cells (APC) 1033 as illustrated in FIG. 3C. After the preparation of the porous scaffolds is completed, the immune cells 1044 may be seeded in bioreactor as shown in FIG. 3D. As shown in FIG. 3D, the immune cells are seeded with the media flow within all sections of the bioreactor and can be found in upper section 122, lower section 126, and middle section 124, within basket 116 as the porous coated scaffolds creates a niche with low shear force that mimic the natural environment of the immune cells and thus allows optimal expansion of immune cells 1044. Additionally, upon exposure to antigens and/or APC immune cells 1044 are activated as previously described above.

In certain embodiments, immune cells 1044 are incubated in bioreactor 100, on APC mimetic scaffold (APC-MS). In further embodiments, the immune cells are subsequently harvested from the porous coated scaffold, for incorporation into a pharmaceutical composition.

In further optional embodiments, the immune cells are seeded with gentle agitation to encourage even distribution, e.g., in the case of a packed bed or solid-state scaffold. In the case of microcarriers, APC-MS and T cells are gently suspended and gently mixed. In either case, after seeding, perfusion and agitation is stopped at least for a period of time to enable interaction between the T cells and the APC-MS, and subsequent activation.

Figure 4:
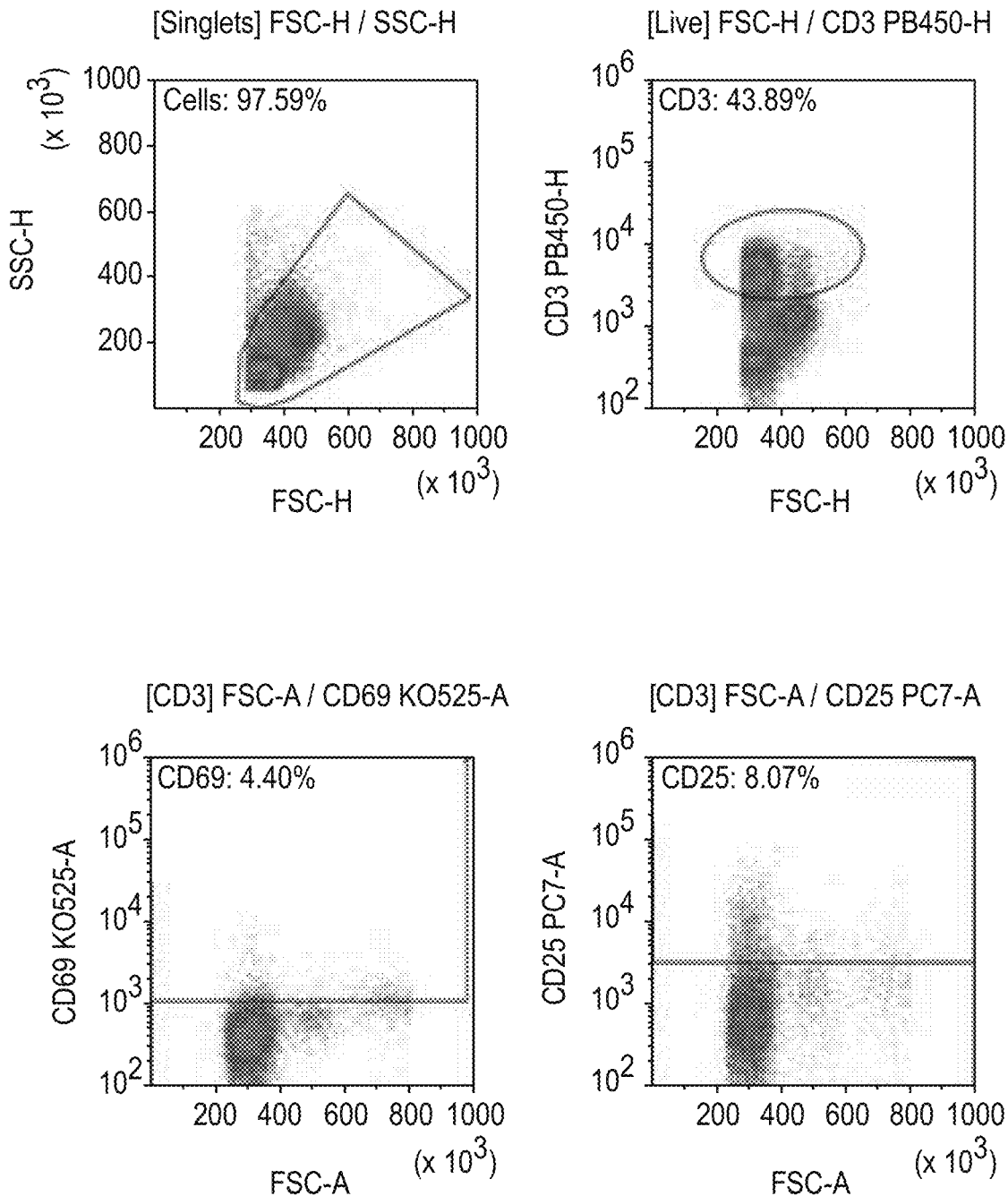
FIG. 4 is a Flow cytometry plot of T-cell activation and proliferation following 7 days growth in a packed bed bioreactor, where activation and proliferation of the cells were measured on days 0, 5 and 7.
Figure 4:
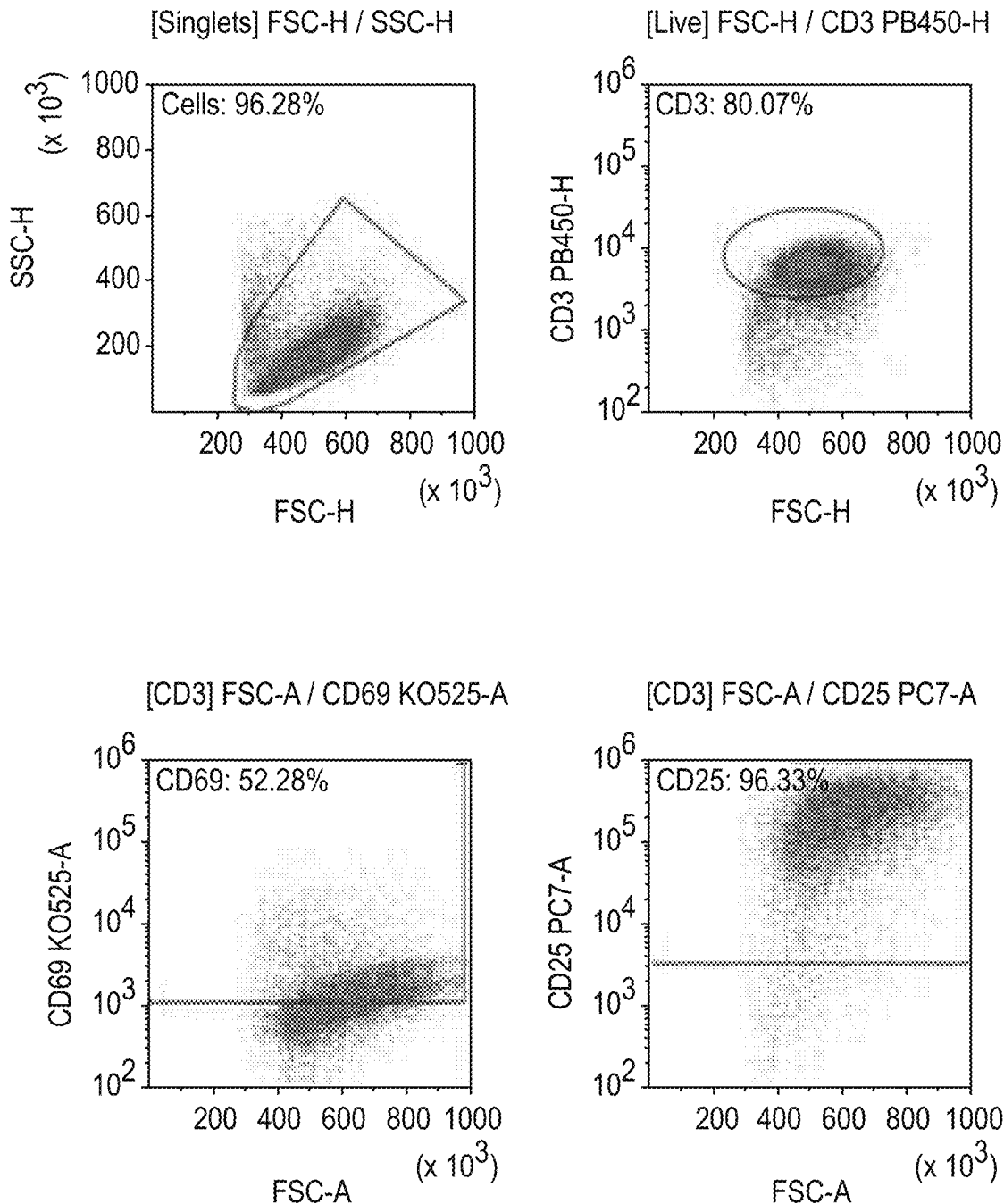
Figure 4:
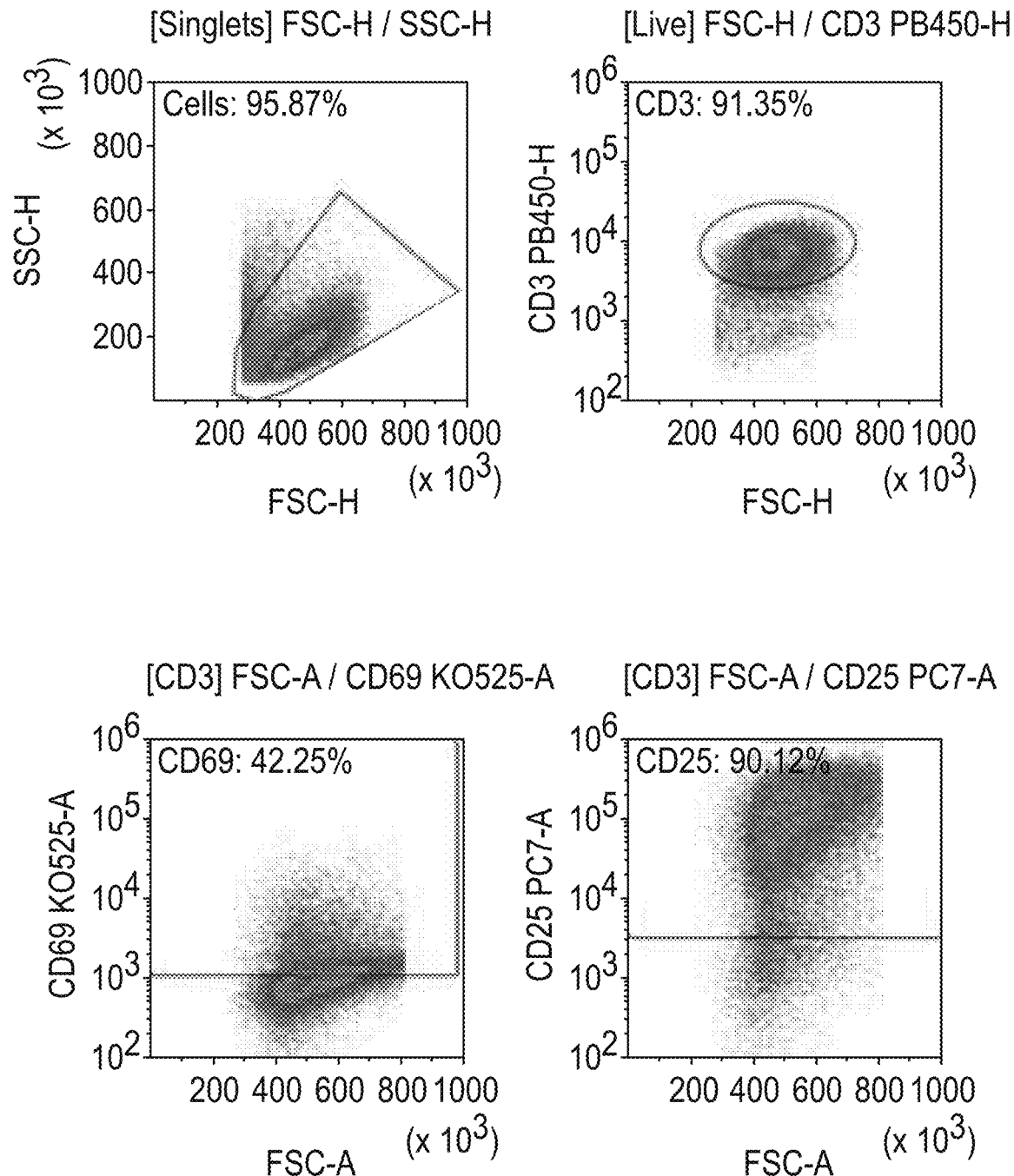
Figure 4:
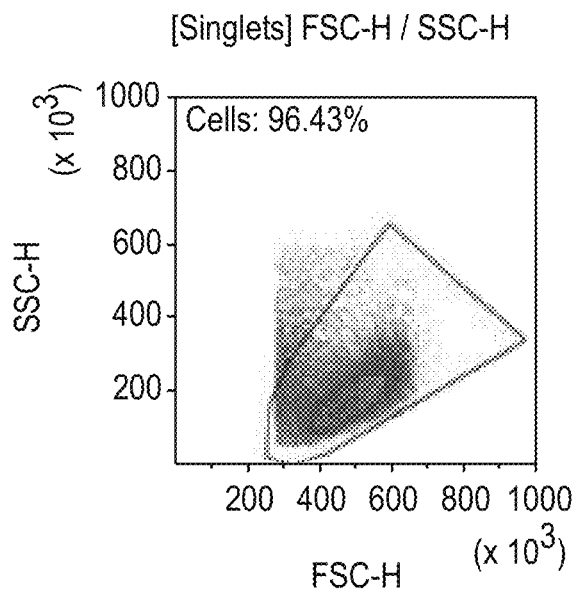
Figure 4:
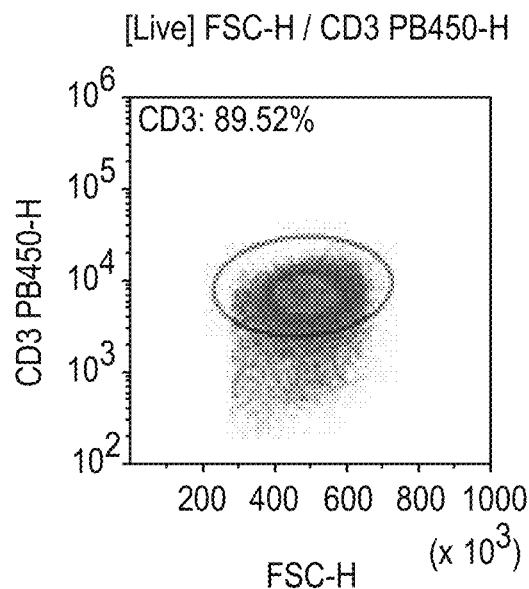
Figure 4:
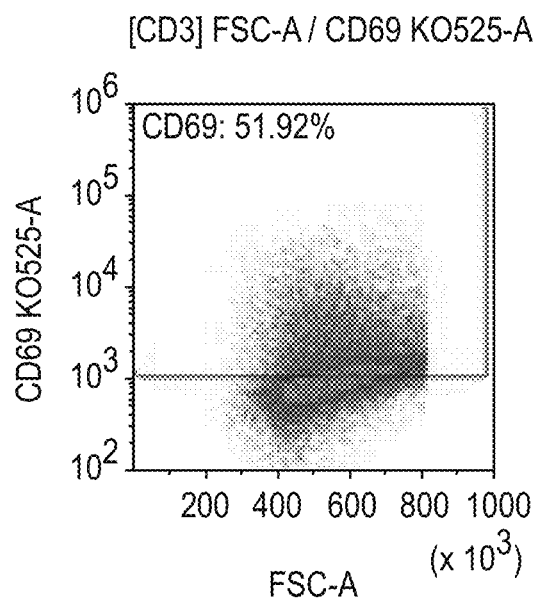
Figure 4:
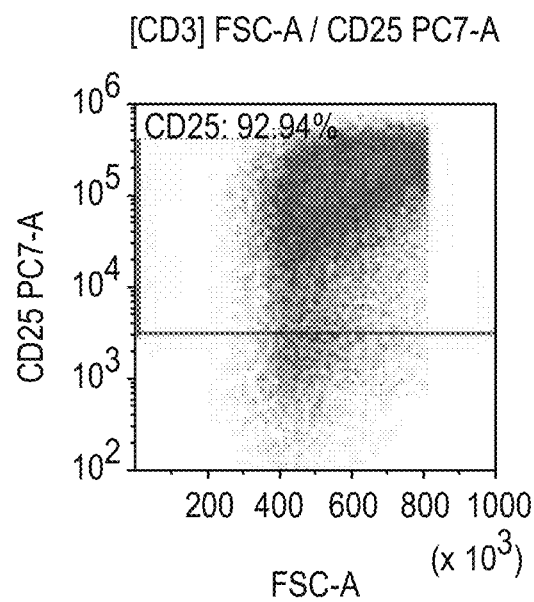

FIG. 4 is a Flow cytometry plot of T-cell activation and proliferation following 7 days of growth in a packed bed bioreactor, where activation and proliferation of the cells were measured on days 0, 5 and 7. The cells population distribution was analyzed by the flow cytometer Cyto-FLEX™ which contains 3 lasers, (405 nm, 488 nm, 638 nm) and 13 channels for fluorescence detection.

PBMCs cells were seeded into the bioreactor packed bed containing Fibra-Cel® carriers with immobilized antibodies provided signals for T-cell activation (both anti-CD3 and anti-CD28 antibodies). The activation of T-cells was assessed on day 0, 5, 7, by measuring CD69 (an inducible cell surface marker expressed upon activation via the TCR) and CD25 ($\alpha$-chain of IL-2 receptor) expression, which are activation markers commonly associated with T-cell activation. The results obtained demonstrated successful stimulation of T-lymphocyte activation and proliferation as presented by increase of CD3 marker from ~44% on day 0, to ~91% on day 7. These results indicated that specifically T lymphocytes were proliferated over the 7-day period. CD69 and CD25 were upregulated from ~4%, ~8%, from day 0 to ~42%, 90% at day 7 indicating activation of T cells. Moreover, following the harvest step on day 7 in the collected sample of all cells no change in cell markers was detected indicating that no other cell population was within the bioreactor. Furthermore, no change in activation markers level was detected suggesting harvesting of the cells did not affect cell status.

CD69, which is an inducible cell surface marker expressed upon activation via the TCR or the IL-2 receptor (CD25). It plays a role in the proliferation and survival of activated T lymphocytes.

Figure 5A:
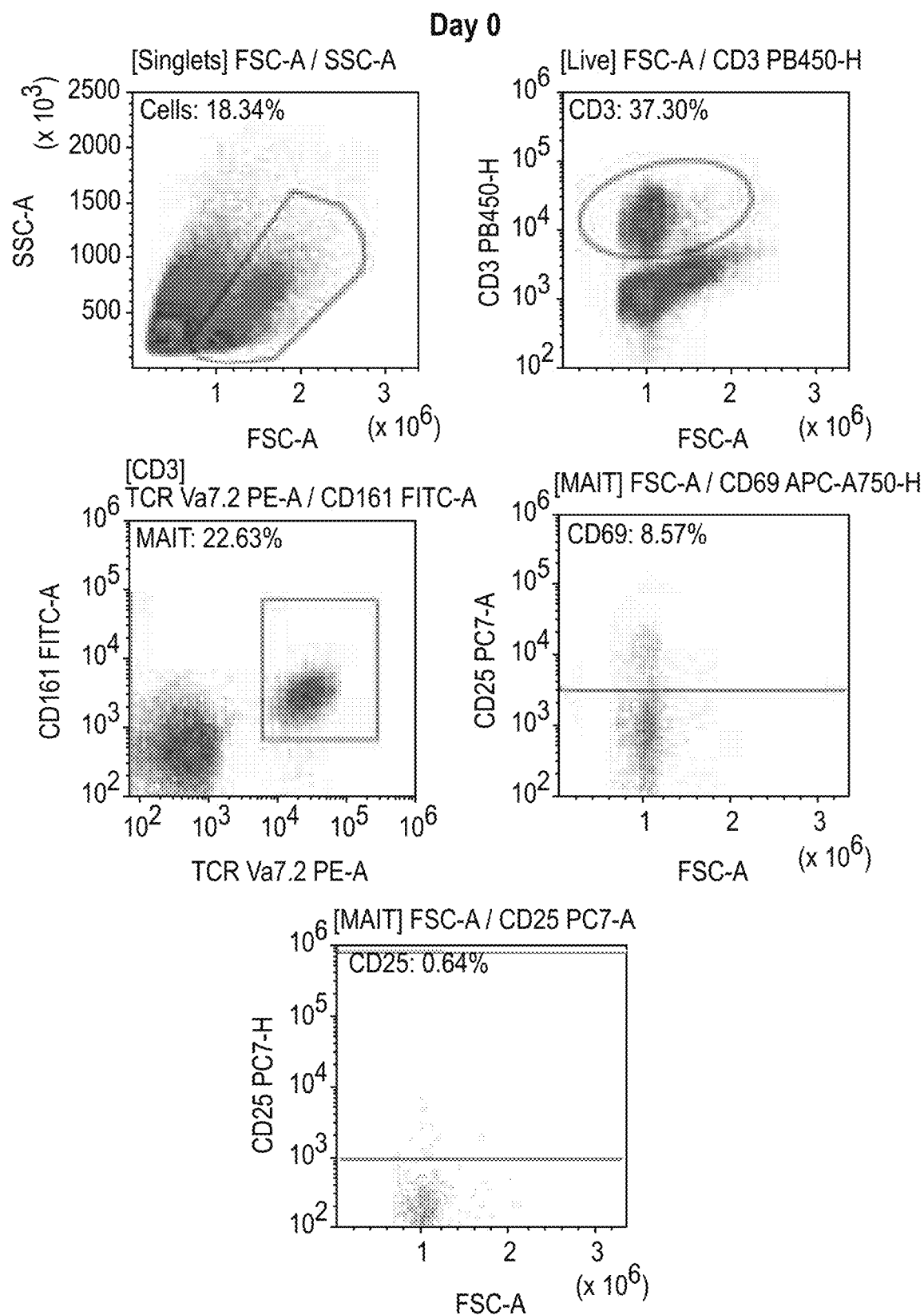
FIG. 5A is a flow cytometric plot of MAIT cell's activation and proliferation for 10 days growth in a packed bed bioreactor, where activation and proliferation of the cells were measured on days 0, 5, 7 and 10.
Figure 5A:
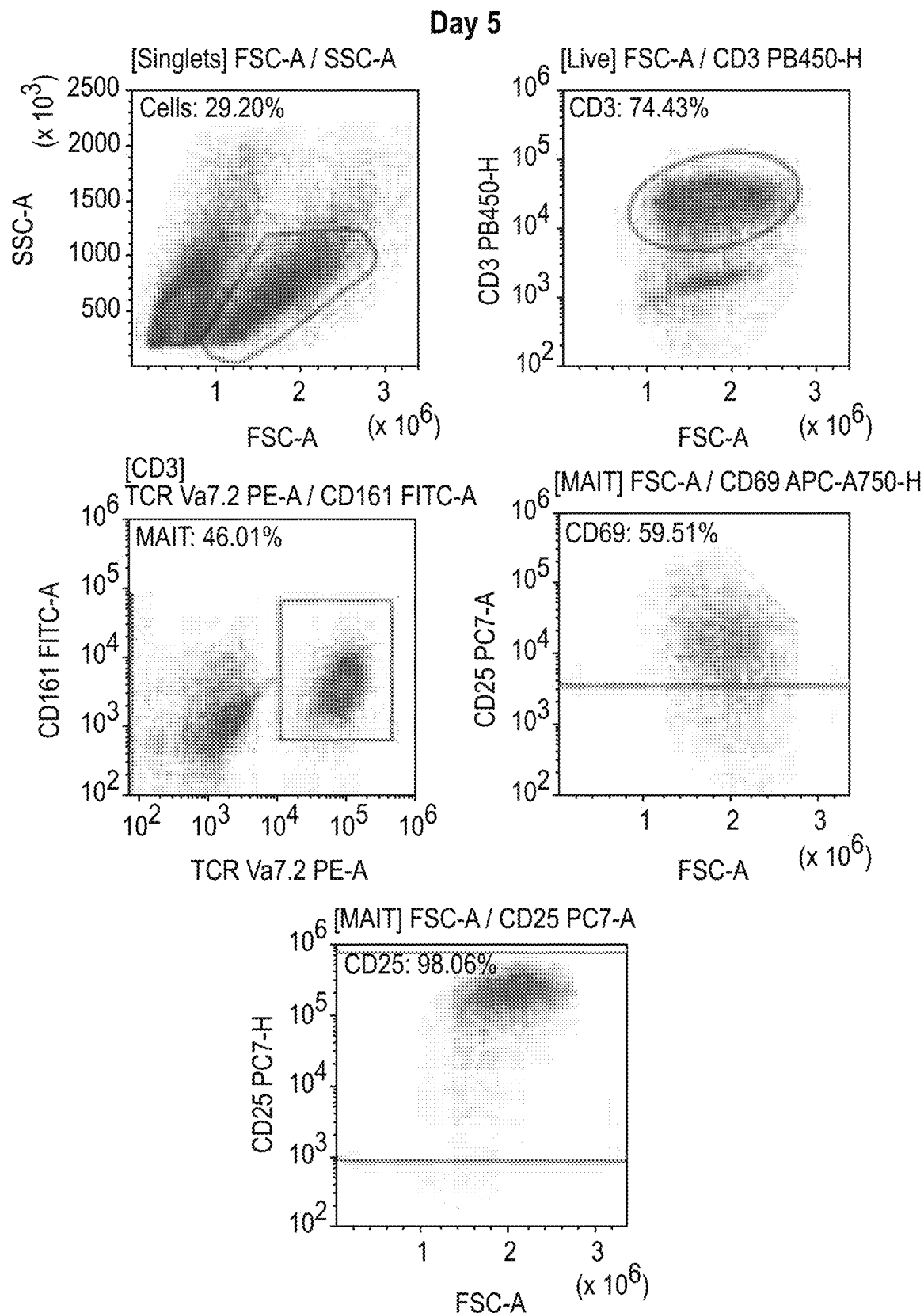
Figure 5A:
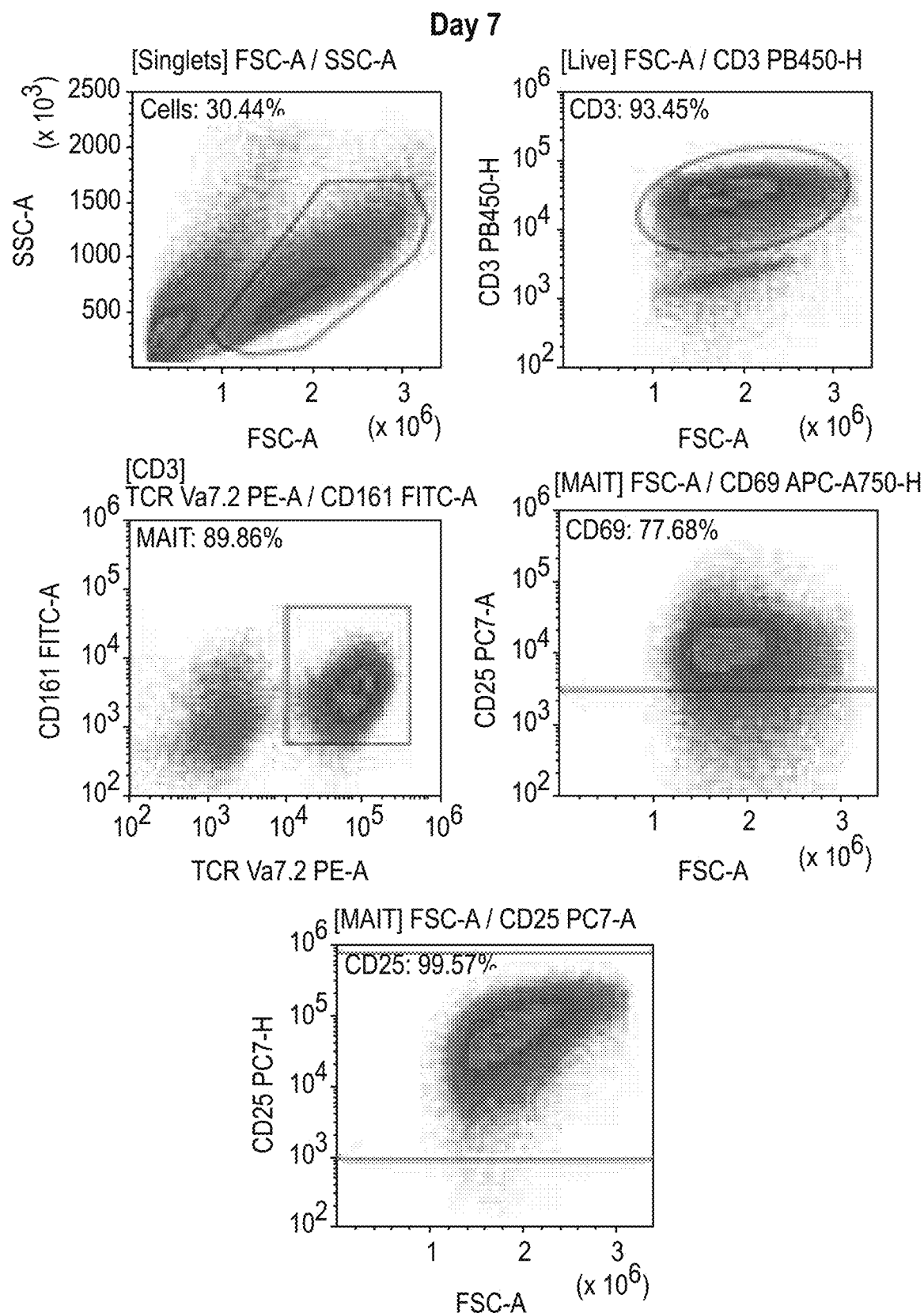
Figure 5A:
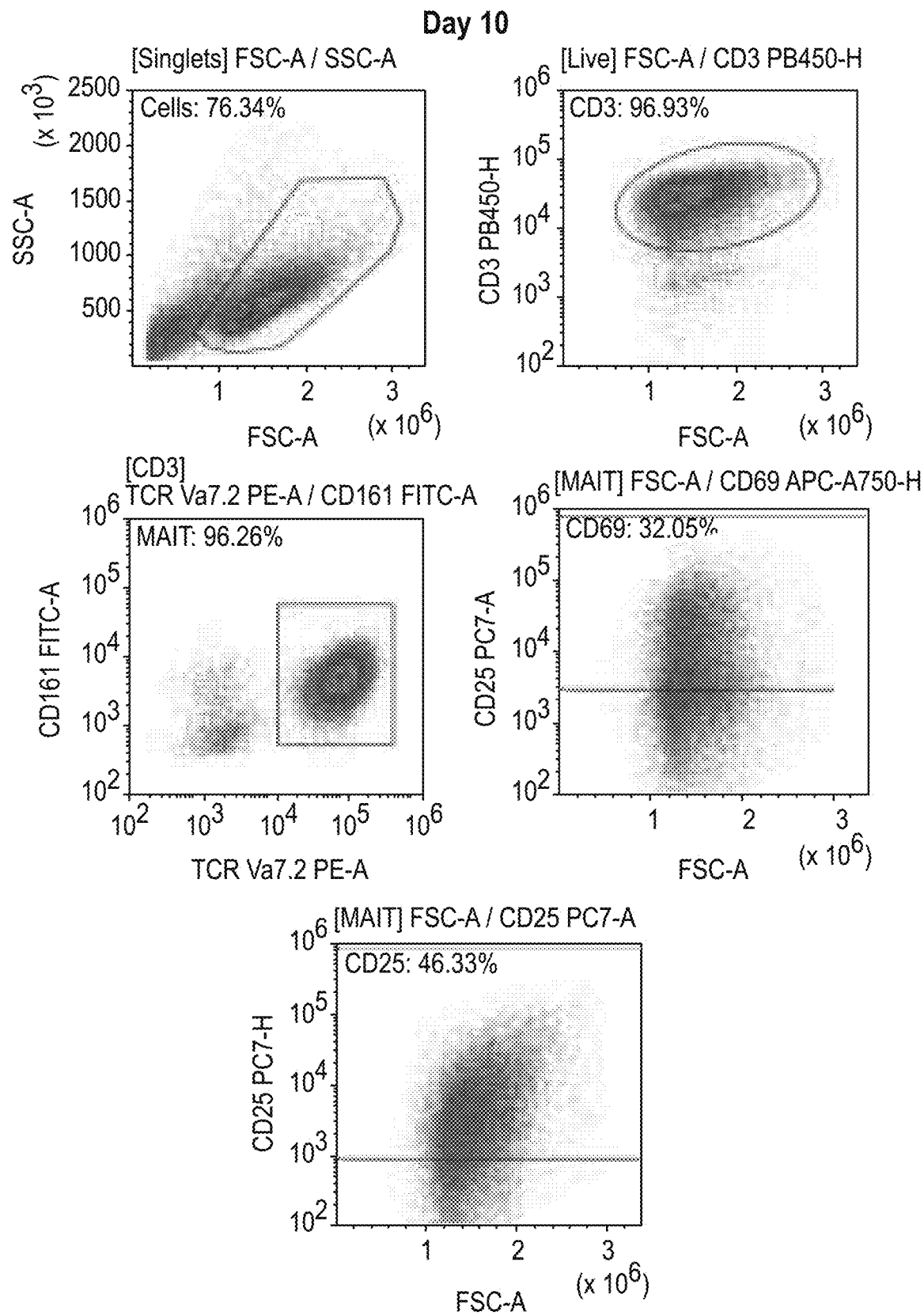

FIG. 5A is a flow cytometric plot of MAIT cell's activation and proliferation for 10 days growth in a packed bed bioreactor, where activation and proliferation of the cells were measured on days 0, 5, 7 and 10. The cells population distribution was analyzed by the flow cytometer Cyto-FLEX™.

IVB's mononuclear cells were seeded into packed bed bioreactor containing ECM-coated Fibra-Cel® carriers which mimic the natural environment and facilitate the attachment of APC's. MAIT cells activation was induced by 5-OP-RU antigen and IL-15. The activation and proliferation of MAIT cell was assessed at several time points: days 0, 5, 7 and 10. MAIT cells population was detected by the expression of CD3, V$\alpha$7.2, CD161 markers. The results presented an increase in the proportion of MAIT cells starting with 22.6% on day 0 and up to 96.26% on day 10. Furthermore, the expression of activation markers CD69 and CD25 was elevated from day 0 to day 7 and decreased by day 10.

Figure 5B:
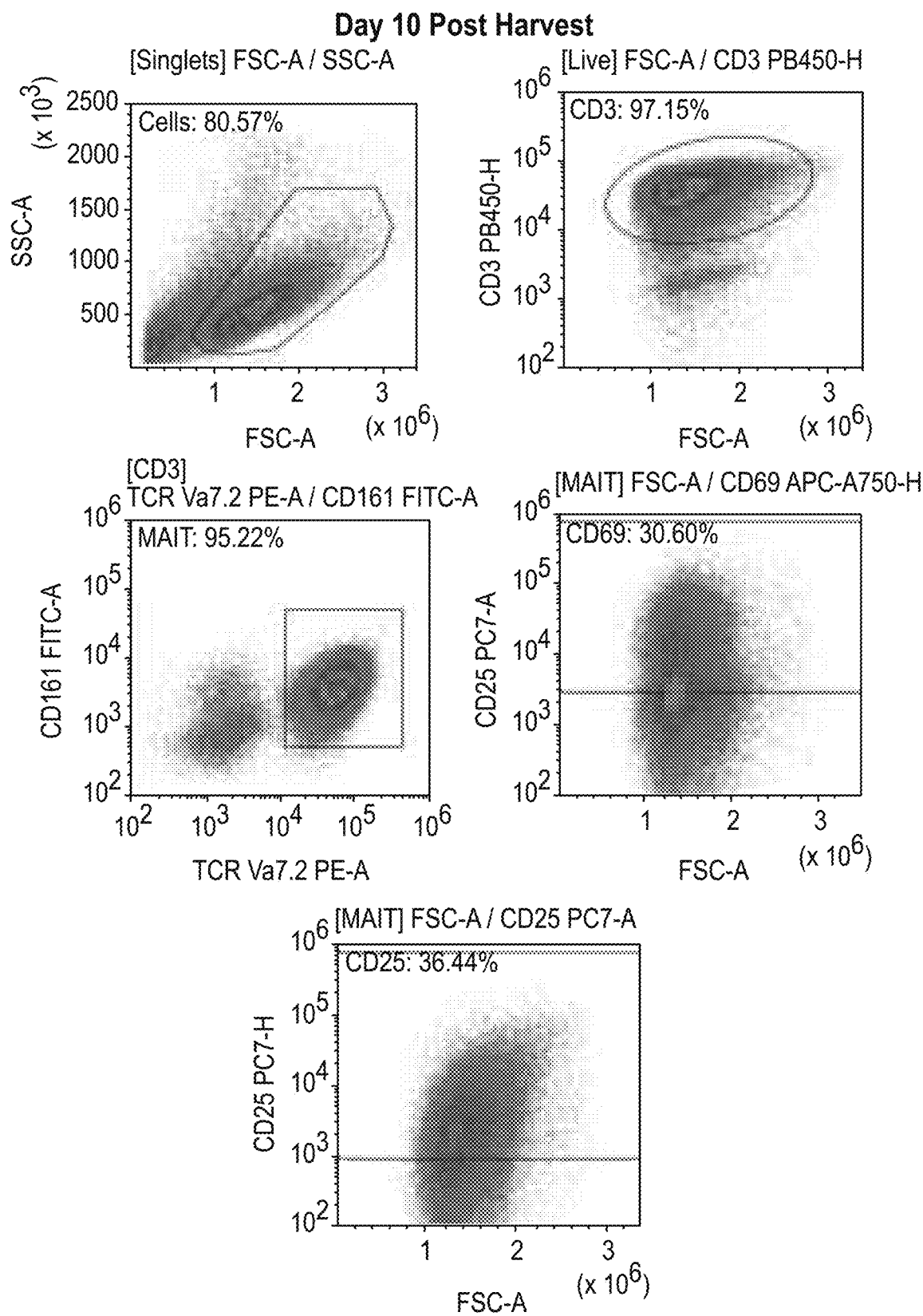
FIG. 5B is a flow cytometric plot of MAIT cells growth following transition of the cells from a first bioreactor to a second bioreactor on day 10 and additional 7 days growth in the second bioreactor.
Figure 5B:
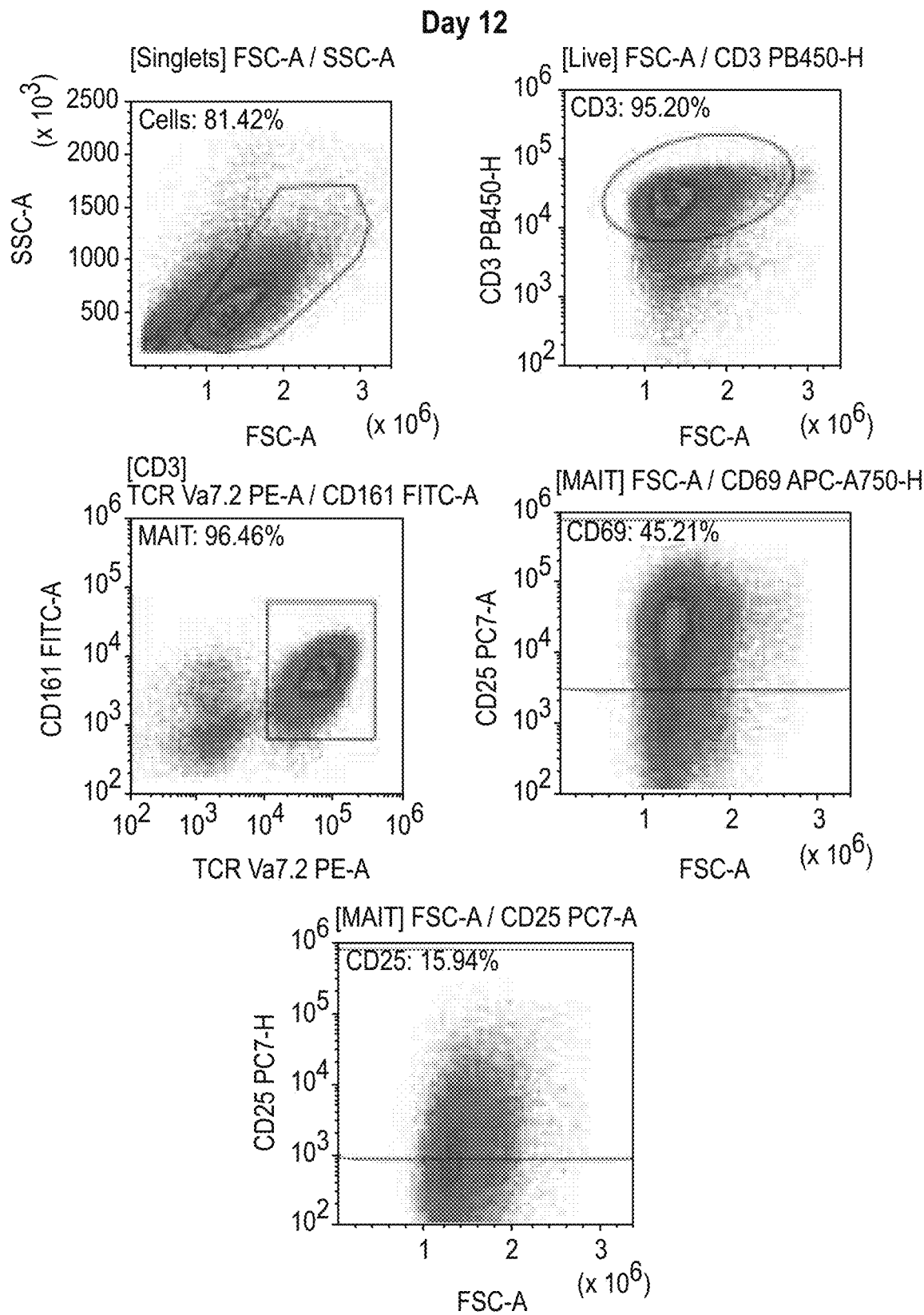
Figure 5B:
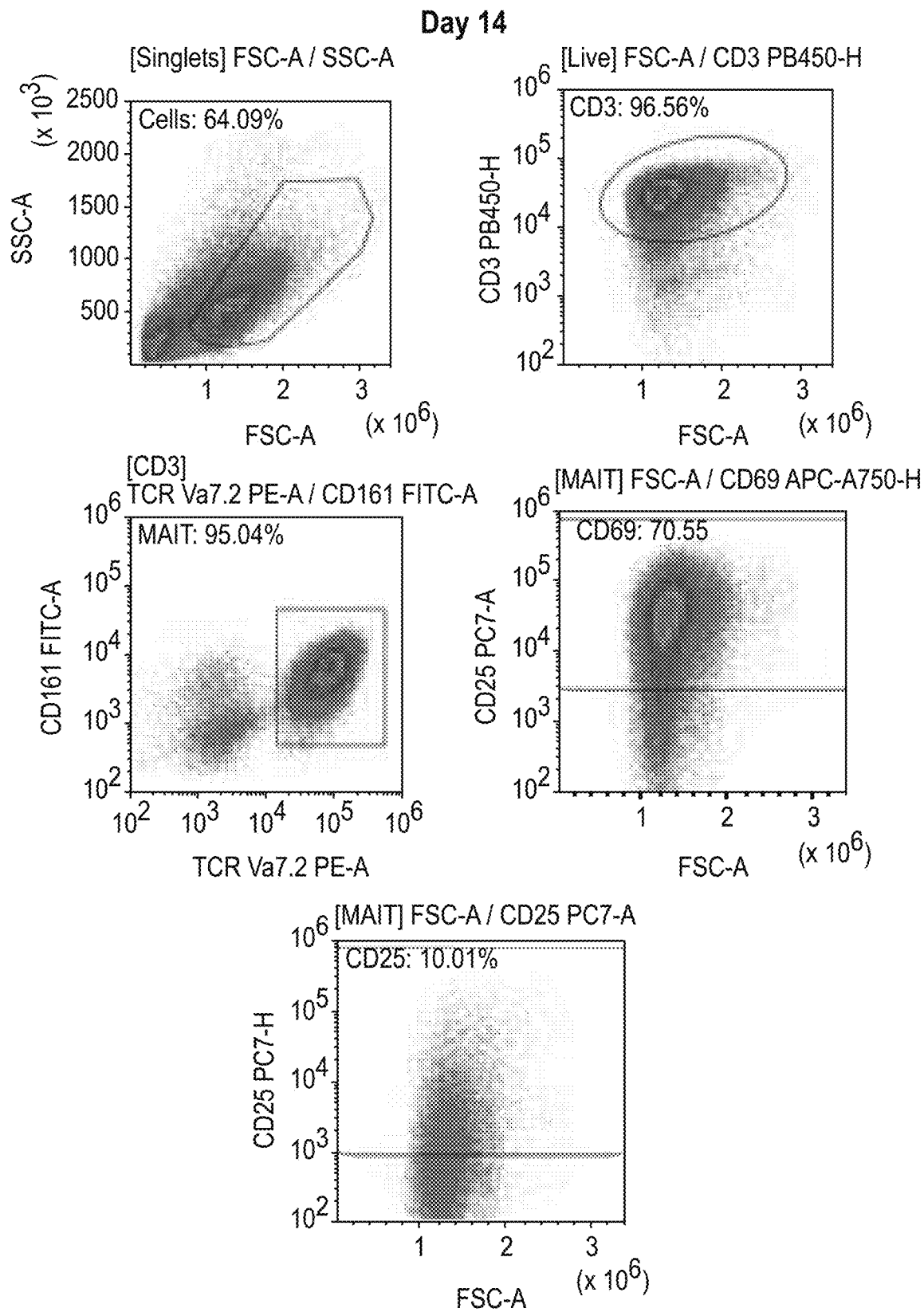
Figure 5B:
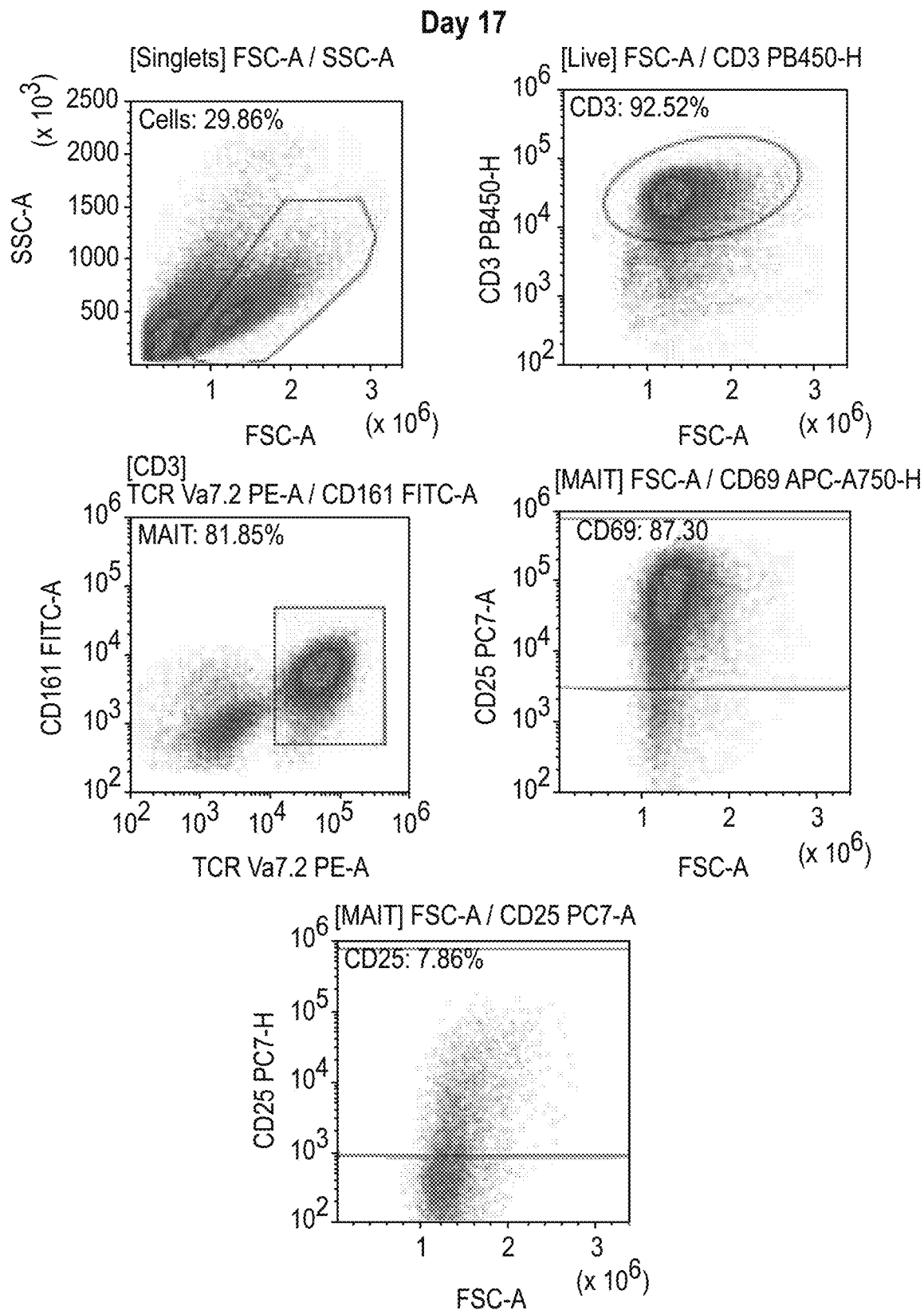

FIG. 5B is a flow cytometric plot of MAIT cells growth following transition of the cells from a first bioreactor to a second bioreactor on day 10 and additional 7 days growth in the second bioreactor. Cells that had reached maximal growth capacity by day 10 in the first bioreactor were harvested, and approximately 30% of these cells were then seeded into a second bioreactor, which was similar in design to the first one. The cells were grown for additional 7 days. Flow cytometry results demonstrated that MAIT percentages were similar during most of the time but presented a decrease from >90% at day 14 to 82% at day 17. CD69 Marker expression was upregulated from 30% to 87% on day 17 indicating that MAIT cells maintained their activation signal, while CD25 gradually reduced as expected.

Figure 6:
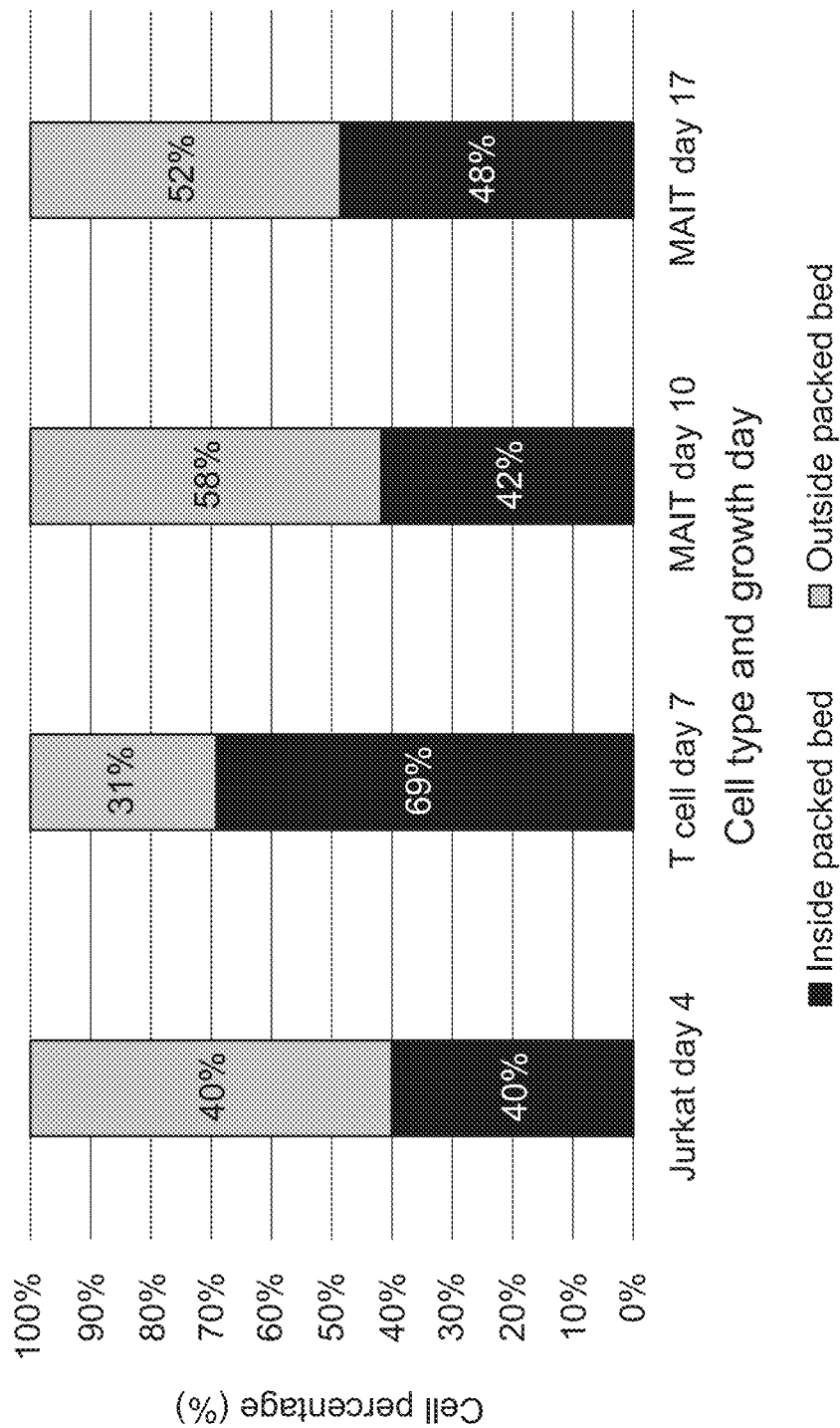
FIG. 6 is a graphic illustration of cells distribution inside and outside the bioreactor packed bed, for three different immune cell types: Jurkat, PBMC's and MAIT cells.

FIG. 6 is a graphic illustration of cells distribution inside and outside the bioreactor packed bed, for three different immune cell types: Jurkat, PBMC's and MAIT cells, in two different growth days. Shown in percentage.

The Fibra-Cel® disk properties and packed bed structure allow the creation of a niche inside the bioreactor system that mimics the cells' natural environment, in which the cells could stay for a while with low shear stress inside. FIG. 6 shows the distribution of cells inside and outside the bioreactor packed bed. The values were calculated according to cells count before and after packed-bed harvest, that was conducted by several wash steps accompanied by packed bed vibration. The results show at least 40% of all viable cells are inside the packed-bed at all three given immune cell types at different packed-bed harvest time points throughout the growth period.

It could be assumed that the following cell distribution models are maintained for the entire cell expansion period, since a significant decrease in cell concentration was observed a few hours after cell seeding.

Figure 7:
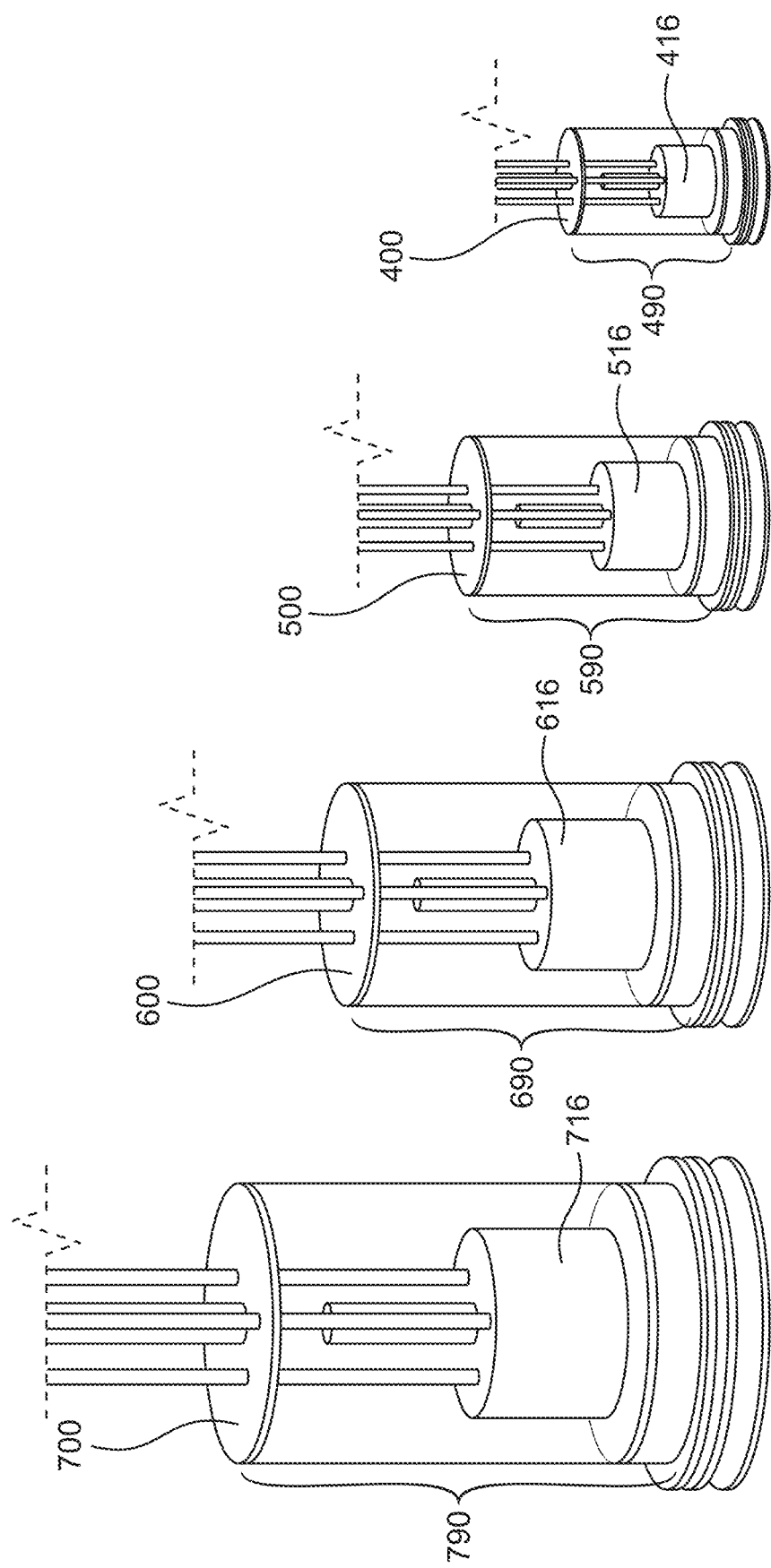
FIG. 7 is a schematic illustration of different size packed bed bioreactors illustrating the high scalability of the system of the invention.

FIG. 7 is a schematic illustration of different size packed bed bioreactors illustrating the high scalability of the system of the invention. In accordance with optional implementation of the invention, the first seeding of the immune cells population may be performed in the mini packed bed bioreactor 400 having mini basket 416, wherein the total maximal volume of mini bioreactor 400 is defined by its container dimensions 490. Upon expansion of the cells in bioreactor 400, the cells or portion of the cells may be reseeded in a bigger sized bioreactor 500 having packed bed basket 516 that is larger than basket 416 and allows larger number of porous scaffolds and higher expansion of cells relative to bioreactor 400, as the total volume of bioreactor 500 is higher and determined by its container dimensions 590. The same process may be performed to a larger bioreactor 600 having basket 616 and container 690, and so on until reaching the biggest bioreactor 700 having the largest basket 716 with container dimensions 790 that allows multiple folds grow of immune cells. In accordance with the methods and examples provided above, one can understand that in each bioreactor the terms of growth and activation of the immune cells population can be similar to the former growth session in the smaller bioreactor, or it may be different. At the end of the process large scale growth of immune cells activated by similar or different activators is obtained.

EXAMPLES

Reference is now made to the following examples, which together with the above descriptions illustrate certain embodiments in a non-limiting fashion.

Example 1

Expansion of Jurkat Cells in a Packed-Bed Bioreactor

A 0.5 L packed bed MiniBio reactor was assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor was connected to Applikon MiniBio control station.

The Fibra-Cel® disks were pre-incubated with RPMI-1640 supplemented with 10% Heat inactivated Fetal Bovine Serum (HI-FBS) and 0.1% 50 mg/ml Gentamicin, for about 24 hours at 37° C., during the incubation the serum proteins interact electrostatically with the hydrophilic end groups on the Fibra-Cel® disks and create an Extracellular Matrix (ECM) coating on the Fibra-Cel®, which mimics cells natural environment.

81.6×10⁶ cells were thawed into RPMI-1640 supplemented with 10% HI-FBS and 0.1% 50 mg/ml Gentamicin, the thawed cells were diluted to a target concentration of 0.24×10⁶ cells/ml at seeding. The prepared cells suspension was seeded into the bioreactor system set to the following conditions: temperature of 37° C., 80% dissolved oxygen (DO), pH 7.4 and agitation of 150 rpm, so that the total volume inside the bioreactor is completed to 340 ml.

On the 3$^{rd}$ day of culture, media was refreshed by 25% (meaning that 25% of fresh media was added). On the 4$^{th}$ day of culture, the cells were harvested from the packed bed bioreactor, due to massive proliferation within a very short period. The total cells number reached 830×10⁶ cells, meaning a fold expansion of 10.4 (results are detailed in table 1). The distribution of the cells inside and outside the packed bed is presented in FIG. 6.

Example 2

Activation, Expansion, and Harvest of Peripheral Blood Mononuclear Cells (PBMCs) in a Packed-Bed Bioreactor.

Peripheral blood mononuclear cells (PBMCs) were isolated from human peripheral blood and separated by filtration and density gradient medium Lymphoprep™ (Ficoll). Red blood cells (erythrocytes) were depleted by RBC X1 lysis buffer. The isolated population were cryopreserved in HI-FBS and Dimethyl sulfoxide (DMSO) freezing solution.

A 0.5 L packed bed MiniBio reactor was assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor was connected to Applikon MiniBio control station.

The Fibra-Cel® disks were coated with monoclonal anti-CD3 (OKT3) antibodies and anti-CD28 (CD28.2) antibodies, both provide a co-stimulatory signal that engages the T cell receptor. The quantity of each activating agent was calculated according to 0.21 µg/cm² diluted in PBS. The final solution was incubated for 3 hours at room temperature (RT) and 1.5 hours at 37° C., at 100 rpm.

The incubation with activating agents followed by a blocking procedure, additional incubation with 1% BSA solution for 1 hour at RT and 100 rpm. Then, drained and washed with PBS for 10 minutes at 150 rpm.

The packed bed bioreactor was then prepared and equilibrated for the culture with growth media, composed of RPMI-1640 supplemented with 10% HI-FBS, 1% Sodium pyruvate (100 mM) and 0.1% 50 mg/ml Gentamicin, for about 24 hours at 37° C. During this incubation the serum proteins interact electrostatically with the hydrophilic end group on the Fibra-Cel® disks and create an ECM coating on the Fibra-Cel®, which mimics cells natural environment.

262×10⁶ cells were thawed into RPMI-1640 supplemented with 10% HI-FBS, 1% Sodium pyruvate (100 mM), IL-2 (100 U/L) and 0.1% 50 mg/ml Gentamicin, the thawed cells were diluted to a target concentration of 0.97×10⁶ cells/ml at seeding. The prepared cells suspension was seeded into the bioreactor system set to the following conditions: temperature of 37° C., 80% DO, pH 7.4 and agitation of 100 rpm, so that the total volume inside the bioreactor is completed to 270 ml. Upon seeding, the cells were distributed within the bioreactor between the packed bed, and the "external" environment, and a decrease in cells concentration was observed 3 hours after seeding.

During the growth period, the growth media and cells suspension (at the "external" environment) were sampled daily to measure pH, cells concentration (by Vi-Cell), cells metabolic activity according to nutrients consumption (by Cedex bio analyzer), and cells population distribution by Flow cytometer (CytoFLEX™).

Medium refreshments were conducted on days 3, 5 and 6 by 5.5, 32 and 20% respectively. On the 7$^{th}$ day of culture, the cells were harvested from the packed bed bioreactor, as the maximal growth capacity has been achieved. The total cells number reached 1073×10⁶, 91% CD3 positive, meaning a fold expansion of 8.5. The proportions of the different cell's populations within the culture and their variation over time are presented in FIG. 4. The distribution of the cells inside and outside the packed bed is presented in FIG. 6.

Example 3

Culture of Mucosal Associated Invariant T Cells (MAIT) in a Packed-Bed Bioreactor: Activation, Expansion, Harvest, Re-Expansion and Second Harvest.

Blood mononuclear cells were isolated from human placental intravenous blood (IVB) and separated by filtration and density gradient medium Lymphoprep™ (Ficoll). Red blood cells (erythrocytes) were depleted by RBC X1 lysis buffer. The isolated population were cryopreserved HI-FBS and Dimethyl sulfoxide (DMSO) freezing solution.

A 0.5 L packed bed MiniBio reactor was assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor was connected to Applikon MiniBio control station.

The Fibra-Cel® disks were incubated with RPMI-1640 supplemented with 10% HI-FBS for about 24 hours at 37° C., during the incubation the serum proteins interact electrostatically with the hydrophilic end group on the Fibra-Cel® disks and create an ECM coating on the Fibra-Cel®, which mimics cells natural environment.

300±20×10⁶ cells were thawed into 4Cell® Nutri-T GMP Medium supplemented with 1% L-Glutamine 200 mM and 0.1% 50 mg/ml Gentamicin, the thawed cells were diluted to a target concentration of 1×10⁶ cells/ml. The prepared cells suspension was seeded into the bioreactor system set to the following conditions: temperature of 37° C., 80% DO, pH 7.4 and agitation of 100 rpm, to a final volume of 300 ml. Upon seeding, the cells were distributed within the bioreactor between the packed bed, and the "external" environment, and a decrease in cells concentration was observed 3 hours after seeding.

3 hours after seeding MAIT cells were activated via their T cell receptor (TCR). Activation pathway through TCR requires co-stimulatory signal that includes a recognition of microbial-derived riboflavin metabolites presented on the MHC Class I-like molecule MR1, and co-stimulation by CD28, TLR agonists, bacterial products, or cytokines.

The initial cells population, isolated from human placental IVB, includes various antigen-presenting cells (APC) such as dendritic cells, monocytes, B cells, that can activate MAIT cells via MR1. 5-OP-RU, which is a microbially-derived riboflavin intermediate, was added to growth media at concentration of 250 nM to be presented by APC on MR1 to a MAIT cell TCR. IL-15 at concentration of 50 ng/ml was also added to the growth media, to stimulate MAIT cells (via IL-15R, expressed on MAIT cells) to produce IFN-γ and release granzyme B and perforin.

During the growth period, the growth media and cells suspension were sampled daily to measure pH, cells concentration (by Vi-Cell), cells metabolic activity according to nutrients consumption (by Cedex™ bio analyzer), and cells population distribution by Flow cytometer (CytoFLEX™).

The cells were grown in the packed bed bioreactor for 10 days, medium refreshments were conducted on days 3, 5 and 7 by 5, 5.2 and 100% respectively. On the 10$^{th}$ day of culture, the cells were harvested from the packed bed bioreactor, as the maximal growth capacity has been achieved. The total cells number reached 1089×10$^6$, 94% MAIT cells (Vα7. 2 positive, CD161 high), meaning a fold expansion of 43.5. The proportions of the different cell populations within the culture and their variation over time are presented in FIG. 5A.

After harvesting the cells from the bioreactor on the 10$^{th}$ day of the culture, further expansion of the cells was examined. An additional 0.5 L packed bed MiniBio reactor was assembled and prepared same as previous, a sterile system containing 2.5 grams of Fibra-Cel® disks, pre-incubated with RPMI-1640 supplemented with 10% HI-FBS for about 24 hours at 37° C., in order to provide ECM coating on the Fibra-Cel® discs and create a natural environment for the re-seeded cells.

After ECM coating, the packed bed bioreactor was pre-equilibrated for the culture with growth media, composed of 4Cell® Nutri-T GMP Medium supplemented with 1% L-Glutamine 200 mM and 0.1% 50 mg/ml Gentamicin. 295×10$^6$ of the harvested cells were seeded into the growth media, diluted to a target concentration of ~1×10$^6$ cells/ml. The prepared cells suspension was seeded into the bioreactor system set to the following conditions: temperature of 37° C., 80% DO, pH 7.4 and agitation of 100 rpm, to a final volume of 300 ml. IL-15 at concentration of 50 ng/ml was added to the growth media to induce the MAIT cells expansion.

During the growth period, the growth media and cells suspension were sampled daily to measure pH, cells concentration (by Vi-Cell), cells metabolic activity according to nutrients consumption (by Cedex bio analyzer), and cells population distribution by Flow cytometer (CytoFLEX™).

The cells were grown in the packed bed bioreactor for 7 additional days, medium refreshments were conducted on days 12 and 14 of culture by 26.5 and 100% respectively. On the 17$^{th}$ day of culture, the cells were harvested from the packed bed bioreactor. The total cells number reached 490×10$^6$, 88% MAIT cells (Vα7. 2 positive, CD161 high), meaning a fold expansion of 1.5. The relative percentage of MAIT cells within the culture and their variation over time is presented in FIG. 5B.

Table 1 below summarizes the initial and final total viable cells, their relative population share and fold expansion during the growth period for three different immune cell types: Jurkat, PBMC's and MAIT:

TABLE 1

| Cells of interest | Initial number of cells [×10$^6$ cells] | Final number of cells [×10$^6$ cells] | Fold expansion | Days of growth |
|---|---|---|---|---|
| Jurkat | 81.6 | 830 | 10.4 | 4 |
| T cells (CD3+) | 261 (44% CD3+) | 1073 (91% CD3+) | 8.5 | 7 |
| MAIT- days 1-10 | 299.37 (8% MAIT) | 1089 (94% MAIT) | 43.5 | 10 |
| MAIT- days 10-17 | 295 (94% MAIT) | 490 (86% MAIT) | 1.5 | 7 |

As shown in the Table, all Fold expansion results are higher than 1, indicating cell expansion for all three given immune cells type, also for the second growth phase of MAIT cell. In addition, table 1 shows the shift in cell population balance which reached to over 94% of the target cell at the end of the examined growth period (T cell after 7 growth days and MAIT cell after 10 growth days). The MAIT second growth period shows a slight decrease in MAIT cell percentage (from 94% to 86%).

Example 4

Expansion, Activation and Harvest of Peripheral Blood Mononuclear Cells (PBMCs)-Derived B Cells in a Packed-Bed Bioreactor.

Peripheral blood mononuclear cells (PBMCs) are isolated from human peripheral blood and separated by filtration and density gradient medium Lymphoprep™ (Ficoll). Red blood cells (erythrocytes) are depleted by RBC X1 lysis buffer. The isolated population is cryopreserved in HI-FBS and Dimethyl sulfoxide (DMSO) freezing solution.

A 0.5 L packed bed MiniBio reactor is assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor is connected to Applikon MiniBio control system.

The Fibra-Cel® disks are coated with Anti-CD40 antibodies, to provide an activation signal. The quantity of the activating agent is calculated according to 1 µg/cm$^2$ diluted in PBS. The final solution is incubated for 3 hours at RT and 1.5 hours at 37° C., at 100 rpm. The incubation with activating agents is followed by a blocking procedure, additional incubation with 1% BSA solution for 1 hour at RT, 100 rpm. Then drained and washed with PBS for 10 minutes at 150 rpm.

The Fibra-Cel® disks are pre-incubated with RPMI 1640 supplemented with 10% HI-FBS and 100 IU/ml penicillin-streptomycin, for about 24 hours at 37° C., during the incubation the serum proteins interact electrostatically with the hydrophilic end groups on the Fibra-Cel® disks and create an ECM coating on the Fibra-Cel®, which mimics cells natural environment.

300×10$^6$ cells are thawed into RPMI 1640, supplemented with 5% Heat inactivated Fetal Bovine Serum (FBS), 2 mM of L-glutamine, 1 mM sodium pyruvate, 50 µM of β-mercaptoethanol, 100 IU/ml penicillin-streptomycin, recombinant human IL-4 (10 ng/ml), and IL-21 (10 ng/ml). The thawed cells are diluted to a target concentration of 1×10$^6$ cells/ml at seeding. The prepared cell suspension is seeded into the bioreactor system set to the following conditions: temperature of 37° C., 80% DO, pH 7.4 and agitation of 100 rpm, so that that the total volume inside the bioreactor is completed to 300 ml. Upon seeding, the cells are distributed within the bioreactor between the packed bed, and the "external" environment surrounding the packed bed basket) are sampled daily to measure pH, cells concentration (by Vi-Cell), cells metabolic activity.

During the growth period, the growth media and cell suspension (at the "external" environment) according to nutrients consumption (by Cedex bio analyzer), and cell population distribution by Flow cytometer (CytoFLEX™).

Medium refreshments are conducted on days 4 and 6 by 50%. On the 8$^{th}$ day of culture, the cells are harvested from the packed bed bioreactor.

Example 5

Activation, Expansion, and Harvest of Peripheral Blood Mononuclear Cells (PBMCs)-Derived iNKT Cells in a Packed-Bed Bioreactor.

Peripheral blood mononuclear cells (PBMCs) are isolated from human Peripheral blood and separated by filtration and density gradient medium Lymphoprep™ (Ficoll). Red blood cells (erythrocytes) are depleted by RBC X1 lysis buffer. The isolated population is cryopreserved in HI-FBS and DMSO freezing solution.

A 0.5 L packed bed MiniBio reactor is assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor is connected to Applikon MiniBio control system.

The Fibra-Cel® disks are pre-incubated with RPMI 1640 supplemented with 10% HI-FBS and 100 IU/ml penicillin-streptomycin, for about 24 hours at 37° C., during the incubation the serum proteins interact electrostatically with the hydrophilic end groups on the Fibra-Cel® disks and create an ECM coating on the Fibra-Cel®, which mimics cells natural environment.

$600 \times 10^6$ cells are thawed into RPMI 1640, supplemented with 10% HI-FBS, 2 mM of L-glutamine, 1 mM sodium pyruvate, 10 mM HEPES buffer solution, 0.1 mM MEM nonessential amino acids, 5.5 µM of β-mercaptoethanol, 100 IU/ml penicillin-streptomycin, and 100 IU/ml recombinant human IL-2. The thawed cells are diluted to a target concentration of $2 \times 10^6$ cells/ml at seeding. The prepared cell suspension is seeded into the bioreactor system set to the following conditions: temperature of 37° C., 80% DO, pH 7.4 and agitation of 100 rpm, so that that the total volume inside the bioreactor is completed to 300 ml. Upon seeding, the cells are distributed within the bioreactor between the packed bed, and the "external" environment. 3 hours after seeding the activation steps begins by spiking the bioreactor medium with 100 ng/ml α-galactosylceramide in order to be presented on CD1d located on antigen presenting cells (from the PBMC population) that are adherent on the Fibra-Cel® disks.

During the growth period, the growth media and cell suspension (at the "external" environment) are sampled daily to measure pH, cells concentration (by Vi-Cell), cells metabolic activity according to nutrients consumption (by Cedex bio analyzer), and cell population distribution by Flow cytometer (CytoFLEX™).

Medium refreshments are conducted on day 3 and 6 by 70%. On the $7^{th}$ day of culture, the cells are harvested from the packed bed bioreactor.

Example 6

Activation, Expansion, and Harvest of Peripheral Blood Mononuclear Cells (PBMCs)-Derived γδT Cells in a Packed-Bed Bioreactor.

Peripheral blood mononuclear cells (PBMCs) are isolated from human Peripheral blood and separated by filtration and density gradient medium Lymphoprep™ (Ficoll). Red blood cells (erythrocytes) are depleted by RBC X1 lysis buffer. The isolated population is cryopreserved in HI-FBS and DMSO freezing solution.

A 0.5 L packed bed MiniBio reactor is assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor is connected to Applikon MiniBio control station.

The Fibra-Cel® disks are pre-incubated with RPMI 1640 supplemented with 10% HI-FBS and 100 IU/ml penicillin-streptomycin, for about 24 hours at 37° C., during the incubation the serum proteins interact electrostatically with the hydrophilic end groups on the Fibra-Cel® disks and create an ECM coating on the Fibra-Cel®, which mimics cells natural environment.

$300 \times 10^6$ cells are thawed into RPMI 1640, supplemented with 10% HI-FBS, 2 mM of L-glutamine, 1 mM sodium pyruvate, 10 mM HEPES buffer solution, 0.1 mM MEM nonessential amino acids, 50 µM of β-mercaptoethanol, 100 IU/ml penicillin-streptomycin and 300 IU/mL of IL-2. The thawed cells are diluted to a target concentration of $1 \times 10^6$ cells/ml at seeding. The prepared cell suspension is seeded into the bioreactor system set to the following conditions: temperature of 37° C., 80% DO, pH 7.4 and agitation of 100 rpm, so that the total volume inside the bioreactor is completed to 300 ml. Upon seeding, the cells are distributed within the bioreactor between the packed bed, and the "external" environment. 3 hours after seeding the activation steps begin by spiking the bioreactor medium with 5 µM of zoledronic acid.

During the growth period, the growth media and cell suspension (at the "external" environment) is sampled daily to measure pH, cells concentration (by Vi-Cell), cells metabolic activity according to nutrients consumption (by Cedex bio analyzer), and cell population distribution by Flow cytometer (CytoFLEX™).

Medium refreshments are conducted on day 4, 7, 10 and 13 by 50%. On the $14^{th}$ day of culture, the cells are harvested from the packed bed bioreactor.

Example 7

Activation, Expansion, and Harvest of Peripheral Blood Mononuclear Cells (PBMCs)-Derived Natural Killer (NK) Cells in a Packed-Bed Bioreactor.

Natural Killer (NK) cells are isolated from human peripheral blood mononuclear cells (PBMCs), using RosetteSep (STEMCELL Technologies; routinely ≥95% CD56+CD3−), and separated by filtration and density gradient medium Lymphoprep™ (Ficoll). Red blood cells (erythrocytes) are depleted by RBC X1 lysis buffer. The isolated population is than cryopreserved in HI-FBS and DMSO freezing solution.

A 0.5 L packed bed MiniBio reactor is assembled, containing 2.5 grams of Fibra-Cel® disks, then sterilized in autoclave by steam sterilization, at temperature of 122.5° C. and pressure of 1 bar over atmosphere pressure for 30 minutes. Afterwards the MiniBio reactor is connected to Applikon MiniBio control station.

The Fibra-Cel® disks are pre-incubated with RPMI 1640 supplemented with 10% HI-FBS and 100 IU/ml penicillin-streptomycin, for about 24 hours at 37° C., during the incubation the serum proteins interact electrostatically with the hydrophilic end groups on the Fibra-Cel® disks and create an Extracellular Matrix (ECM) coating on the Fibra-Cel®, which mimics cells natural environment.

$900 \times 10^6$ NK cells are thawed into RPMI 1640, supplemented with 10% HI-FBS, 2 mM of L-glutamine, 1 mM sodium pyruvate, 10 mM HEPES buffer solution, 0.1 mM MEM nonessential amino acids, 100 IU/ml penicillin-streptomycin. The thawed cells are diluted to a target concentration of $3 \times 10^6$ cells/ml at seeding. The prepared cell suspension is seeded into the bioreactor system set to the following conditions: temperature of 37° C., 80% DO, pH 7.4 and agitation of 100 rpm, so that that the total volume inside the bioreactor is completed to 300 ml. Upon seeding, the cells are distributed within the bioreactor between the packed bed, and the "external" environment. For pre-activation the medium is supplemented with recombinant human IL-12 (10 ng/mL), IL-18 (50 ng/mL) and IL-15 (50 ng/mL) and cultured for 16±2 hours, followed by washing steps, and then cultured in growth medium, supplemented with recombinant human IL-15 (1 ng/ml).

During the growth period, the growth media and cell suspension (at the "external" environment) are sampled daily to measure pH, cells concentration (by Vi-Cell), cells metabolic activity according to nutrients consumption (by Cedex bio analyzer), and cell population distribution by Flow cytometer CytoFLEX™).

Medium refreshments are conducted on day 4, and 7 by 30%. On the $8^{th}$ day of culture, the cells are harvested from the packed bed bioreactor.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace alternatives, modifications and variations that fall within the spirit and broad scope of the claims and description. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the invention.

The invention claimed is:

1. A three-dimensional (3D) bioreactor for large scale expansion of immune cells, the 3D bioreactor comprising:
    at least one packed bed chamber;
    at least one porous scaffold surrounded by said at least one packed bed chamber, wherein said at least one porous scaffold is coated with one or more extra cellular matrix protein (ECM) and coated or linked with at least one immune cell activator;
    at least one container surrounding said at least one packed bed chamber;
    a fluid media having at least one population of immune cells suspended in said fluid media contained in said at least one container; and
    at least one gene modifying agent spiked into the fluid media for genetically modifying immune cells inside the 3D bioreactor;
    wherein said fluid media having at least one population of immune cells suspended in said fluid media flows through said packed bed chamber and said at least one porous scaffold coated with one or more ECM causing said expanded immune cells to be further activated within said at least one packed bed chamber upon exposure of said population of immune cells to said at least one porous scaffold coated with one or more ECM coated or linked with at least one immune cell activator.

2. The 3D bioreactor according to claim 1, wherein said immune cell activator is either one of an Antigen Presenting Cell (APC) either loaded with antigen or unloaded with antigen or an antigen conjugated directly to said at least one porous scaffold coated with one or more ECM.

3. The 3D bioreactor according to claim 1 wherein said expanded immune cells are further activated within said at least one packed bed chamber upon exposure to a suspended soluble immune cell activator and further expanded with said at least one porous scaffold coated with one or more ECM.

4. The 3D bioreactor according to claim 1, wherein said at least one population of immune cells are either harvested or reactivated upon exposing an Antigen Presenting Cell (APC) attached to said at least one porous scaffold coated with one or more ECM to an antigen, so as to create additional activation signal to said population of immune cells.

5. The 3D bioreactor according to claim 1, wherein said at least one population of immune cells are either harvested or reactivated by transferring the expanded immune cells to a different bioreactor comprising at least one porous scaffold coated with a different or similar immune cell activator.

6. The 3D bioreactor according to claim 1, wherein said at least one porous scaffold coated with one or more ECM is either a single porous scaffold matrix expanded within an inner space of said at least one packed bed chamber, or a plurality of mini or micro porous scaffolds filling said at least one packed bed chamber.

7. The 3D bioreactor according to claim 1, wherein said fluid media further comprises one or more gene modifying agents capable of genetically modifying said population of immune cells suspended in said fluid media.

8. A method for large scale expansion of immune cells in a three-dimensional (3D) bioreactor, the method comprising the steps of:
    a. inserting at least one porous scaffold into at least one packed bed chamber;
    b. coating said at least one porous scaffold with one or more extra cellular matrix protein (ECM) and coating or linking said at least one porous scaffold with at least one immune cell activator;
    c. circulating a fluid media having at least one population of immune cells suspended in said fluid media contained in at least one container surrounding said at least one packed bed chamber, said fluid media having at least one population of immune cells suspended in said fluid media flows through said at least one packed bed chamber and said at least one porous scaffold coated with one or more ECM; and
    d. genetically modifying the immune cells inside the 3D bioreactor using gene modifying agents spiked into the fluid media and exposing the immune cells population to said at least one activator;
    wherein said at least one porous scaffold coated with one or more ECM has a porosity which allows expansion of said at least one population of immune cells that flows said at least one porous scaffold coated with one or more ECM in large scale without immobilizing said at least one population of immune cells.

9. The method according to claim 8, further comprising a step of harvesting said immune cell population, or a portion thereof, and further expanding and reactivating said harvested immune cell population either in the same at least one 3D bioreactor or in a different bioreactor.

10. The method according to claim 9, further comprising a step of harvesting said immune cell population, or a portion thereof, and further expanding and reactivating said harvested immune cell population either in the same at least one 3D bioreactor or in a different bioreactor.

11. The method according to claim 8, further comprising a step of harvesting said immune cell population, or a portion thereof, and further expanding and reactivating said harvested population of immune cells either in the same at least one 3D bioreactor or in a different bioreactor.

12. The method according to claim 11, further comprising a step of harvesting said population of immune cells followed by a step of genetically modifying said harvested population of immune cells outside said at least one 3D bioreactor and reseeding said genetically modified harvested population of immune cells into the same at least one 3D bioreactor or in a different bioreactor.

13. A three-dimensional (3D) bioreactor for large scale expansion and activation of immune cells population the 3D bioreactor comprising:

at least one packed bed chamber;

at least one porous Antigen Presenting Cell Mimetic Scaffold (APC-MS) surrounded by said at least one packed bed chamber wherein said at least one porous APC-MS is coated with one or more extra cellular matrix protein (ECM) and coated or linked with at least one immune cell activator;

at least one container surrounding said at least one packed bed chamber;

a fluid media having at least one population of immune cells suspended in said fluid media contained in said at least one container; and at least one gene modifying agent spiked into the fluid media for genetically modifying immune cells inside the 3D bioreactor;

wherein said fluid media having at least one population of immune cells suspended in said fluid media flows through said at least one porous APC-MS coated with one or more ECM causing said expanded immune cells to be further activated within said at least one packed bed chamber upon exposure of said population of immune cells to said at least one porous scaffold coated with one or more ECM coated or linked with at least one immune cell activator; and wherein said at least one porous APC-MS coated with one or more ECM has a porosity which allows large scale expansion and/or activation of said at least one population of immune cells that flow through said at least one porous APC-MS coated with one or more ECM without immobilizing said at least one population of immune cells.

14. The 3D bioreactor according to claim 13, wherein said at least one porous APC-MS coated with one or more ECM is either a single unit expanded within an inner space of said at least one packed bed chamber, or a plurality of mini/micro porous APC-MS filling said at least one packed bed chamber.

* * * * *